(12) United States Patent
Bovetto et al.

(10) Patent No.: US 9,387,158 B2
(45) Date of Patent: *Jul. 12, 2016

(54) COSMETIC USE OF WHEY PROTEIN MICELLES

(75) Inventors: Lionel Jean Rene Bovetto, Larringes (FR); Christophe Joseph Etienne Schmitt, Servion (CH)

(73) Assignee: Nestec S.A., Vevey (CH)

( * ) Notice: Subject to any disclaimer, the term of this patent is extended or adjusted under 35 U.S.C. 154(b) by 931 days.

This patent is subject to a terminal disclaimer.

(21) Appl. No.: 12/294,447

(22) PCT Filed: Mar. 26, 2007

(86) PCT No.: PCT/EP2007/052889
§ 371 (c)(1),
(2), (4) Date: Sep. 25, 2008

(87) PCT Pub. No.: WO2007/110419
PCT Pub. Date: Oct. 4, 2007

(65) Prior Publication Data
US 2010/0221295 A1  Sep. 2, 2010

(30) Foreign Application Priority Data

Mar. 27, 2006  (EP) .................................... 06006299

(51) Int. Cl.
*A61K 8/64* (2006.01)
*A61Q 19/00* (2006.01)
*A61K 8/02* (2006.01)
*A61Q 5/02* (2006.01)
*A61Q 19/10* (2006.01)

(52) U.S. Cl.
CPC ................. *A61K 8/64* (2013.01); *A61K 8/0291* (2013.01); *A61Q 19/00* (2013.01); *A61K 2800/28* (2013.01); *A61Q 5/02* (2013.01); *A61Q 19/10* (2013.01)

(58) Field of Classification Search
CPC ....................................................... A61K 8/02
See application file for complete search history.

(56) References Cited

U.S. PATENT DOCUMENTS

| | | | | | |
|---|---|---|---|---|---|
| 4,209,503 | A | * | 6/1980 | Shah et al. | 424/49 |
| 4,734,287 | A | * | 3/1988 | Singer et al. | 426/41 |
| 5,053,219 | A | * | 10/1991 | Giddey et al. | 424/63 |
| 5,427,769 | A | | 6/1995 | Berrocal et al. | 424/54 |
| 5,833,953 | A | | 11/1998 | Berrocal et al. | 424/49 |
| 5,882,705 | A | * | 3/1999 | Sato et al. | 426/41 |

(Continued)

FOREIGN PATENT DOCUMENTS

| | | | |
|---|---|---|---|
| DE | 197 18 848 A1 | | 4/1998 |
| DE | 19718848 A1 | * | 4/1998 |

(Continued)

OTHER PUBLICATIONS

International Search Report and Written Opinion of the International Searching Authority, Application No. PCT/EP2007/052889, dated Jul. 16, 2007.

(Continued)

*Primary Examiner* — Cherie M Stanfield
(74) *Attorney, Agent, or Firm* — K&L Gates LLP

(57) ABSTRACT

The present invention relates to use of whey protein micelles as a cosmetic agent or abrasive agents, and in particular to the use of such micelles in cosmetic compositions as well as to a method for obtaining such compositions.

25 Claims, 20 Drawing Sheets

Mixing ratio < 5:1
Single WPM
Single SBO

Mixing ratio = 5:1
Monolayer coated WPM
Over-aggregation

Mixing ratio > 5:1
Bilayer SBO coated WPM

(56) References Cited

U.S. PATENT DOCUMENTS

| | | | |
|---|---|---|---|
| 6,036,966 A | 3/2000 | Youssefyeh | 424/401 |
| 2007/0231453 A1 | 10/2007 | Bovetto et al. | 426/656 |
| 2009/0035437 A1 | 2/2009 | Bovetto et al. | 426/588 |
| 2009/0136643 A1 | 5/2009 | Bovetto et al. | 426/565 |
| 2009/0162485 A1 | 6/2009 | Schmitt et al. | 426/72 |

FOREIGN PATENT DOCUMENTS

| | | |
|---|---|---|
| FR | 2 655 544 A1 | 6/1991 |
| JP | 57054108 A | 3/1982 |
| JP | 63024857 A | 2/1988 |
| JP | 63135326 A2 | 6/1988 |
| JP | H02502461 T | 8/1990 |
| JP | 07075498 A | 3/1995 |
| JP | 08134497 A | 5/1996 |
| JP | 09002928 A2 | 1/1997 |
| JP | 09238614 A | 9/1997 |
| JP | 2001097842 A2 | 4/2001 |
| JP | 2006217689 A | 8/2006 |
| JP | 2009531043 T | 9/2009 |
| WO | WO 8905136 A1 | 6/1989 |
| WO | WO 03/000215 A1 | 1/2003 |
| WO | WO 2006/034857 A2 | 4/2006 |
| WO | WO 2007/110181 A2 | 10/2007 |
| WO | WO 2007/110411 A2 | 10/2007 |
| WO | WO 2007/110421 A2 | 10/2007 |
| WO | WO 2007/110422 A2 | 10/2007 |

OTHER PUBLICATIONS

European Search Report, application No. EP 06006299, dated Aug. 24, 2006.

* cited by examiner

US 9,387,158 B2

COSMETIC USE OF WHEY PROTEIN MICELLES

This application is a 371 filing of International Patent Application PCT/EP2007/052889 filed Mar. 26, 2007.

FIELD OF THE INVENTION

The present invention relates to the use of whey protein micelles as abrasive agents, in particular in cosmetic compositions and to a method for obtaining said compositions.

BACKGROUND

Heterogeneous compositions containing abrasive agents such as granular pastes or grainy liquids are commonly used in the field of healthcare and cosmetics.

Patent application WO 03000215 discloses for instance toothpaste composition containing as an abrasive agent, inorganic powders, in order to remove the protein film that forms on teeth surfaces.

U.S. Pat. No. 6,036,966 is concerned with topical compositions containing a slightly abrasive powdery component selected from inorganic powders, metal soaps or organic powders such as microcrystalline cellulose for retexturising skin.

There are still many unexplored areas in the field of granular products and their uses.

It is therefore an object of the present invention to provide an alternative to the abrasive media used in the art.

SUMMARY OF THE INVENTION

Accordingly, this object is achieved by means of the features of the independent claims. The dependent claims develop further the central idea of the present invention.

To achieve this object, generally the use of proteins, e.g. the use of whey protein micelles or aggregates containing whey protein micelles as abrasive medium is proposed. In particular, the present invention relates to the topical use of whey protein micelles.

In a further aspect of the invention, a cosmetic composition comprising whey protein micelles is provided.

A third aspect of the invention relates to a process for the manufacture of a cosmetic composition.

A still further aspect relates to a product obtainable by such process.

FIGURES

The present invention is further described hereinafter with reference to some preferred embodiments shown in the accompanying figures in which.

Figure 6:
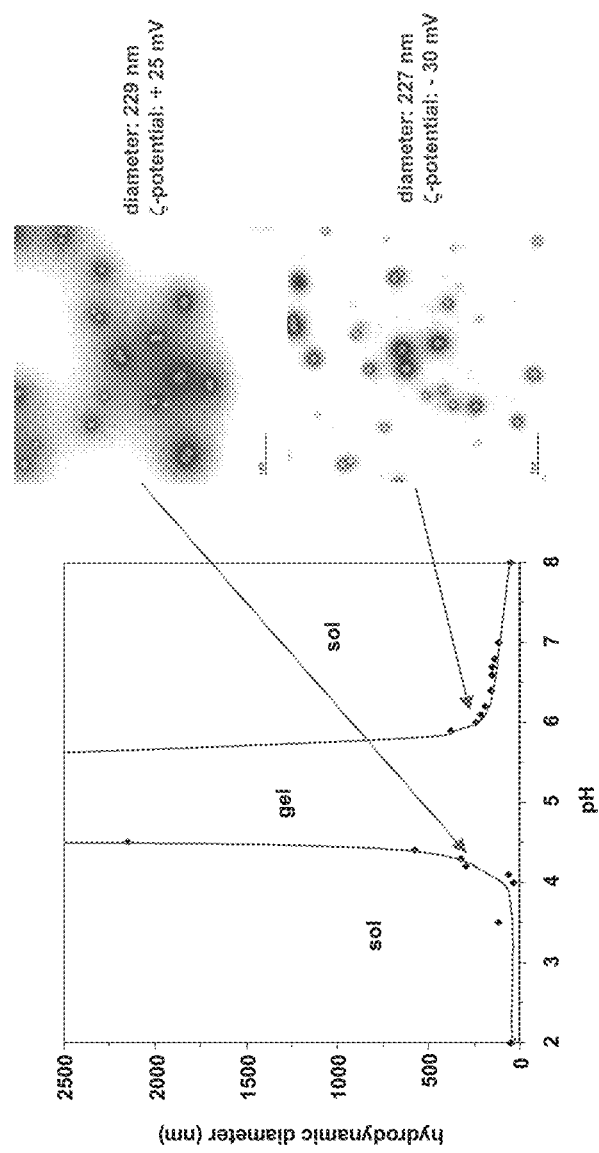

FIG. 6 shows the intensity-based equivalent hydrodynamic diameter of whey protein obtained by heat-treatment of a 1 wt % β-lactoglobulin dispersion for 15 min at 85° C. at pH ranging from 2 to 8. Whey protein micelles are obtained at pH 4.25 (positively charged with a zeta potential around +25 mV) and at pH 6.0 (negatively charged with a zeta potential around—30 mV). Z-averaged hydrodynamic diameter of the micelles was 229.3 nm at pH 4.25 and 227.2 nm at pH 6.0. The corresponding micrographs of the micelles obtained by TEM after negative staining are shown. Scale bars are 1 μm.

Figure 7:
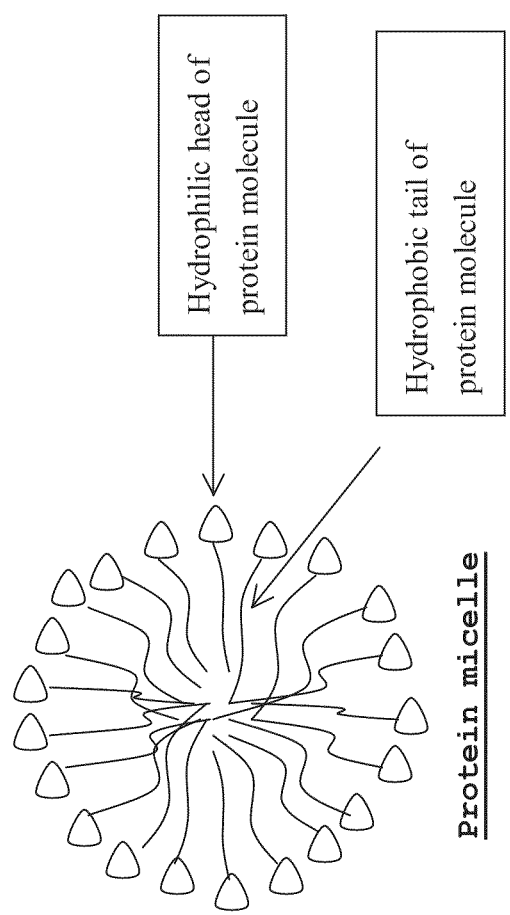

FIG. 7 shows a highly schematic structure of a whey protein micelle.

Figure 8:
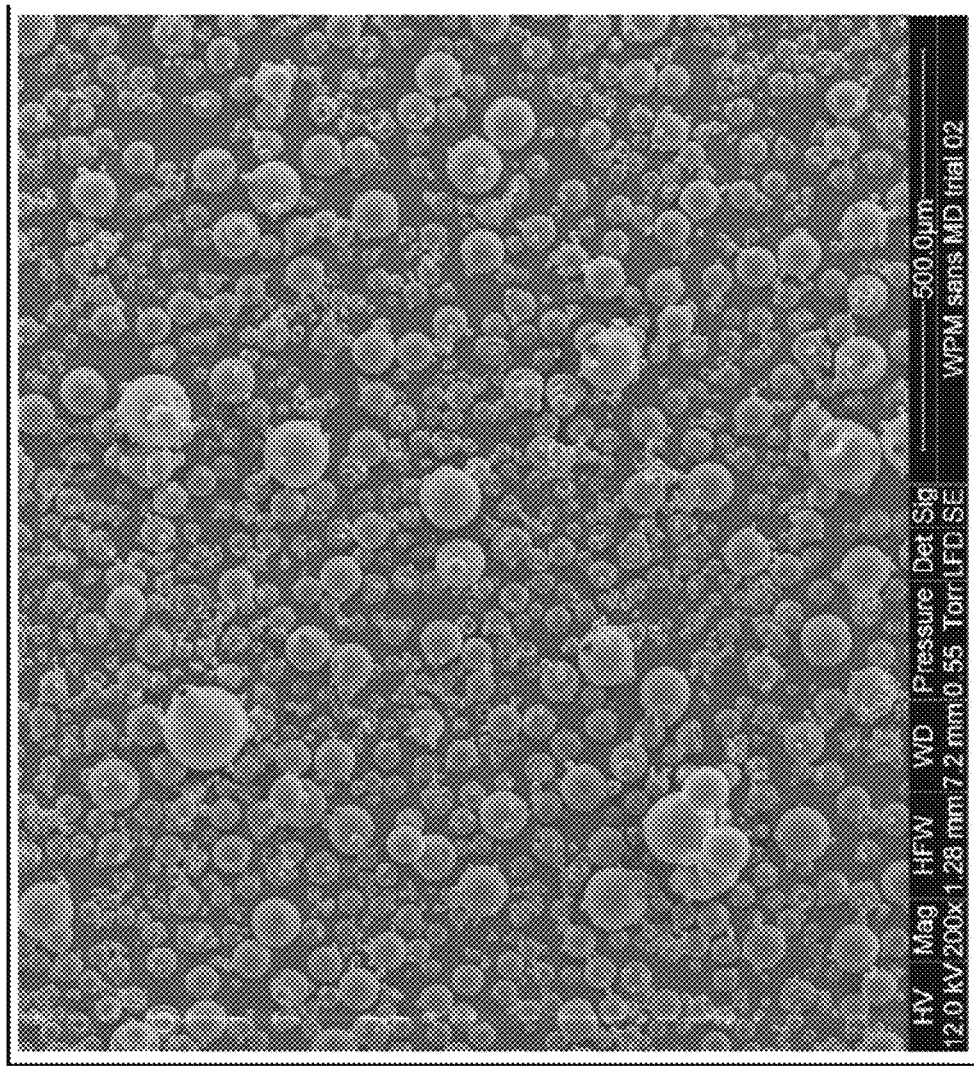

FIG. 8 shows a SEM (Scanning electron microscopy) micrograph of a whey protein micelle powder obtained after spray drying of a 20% protein content dispersion after microfiltration.

Figure 9:
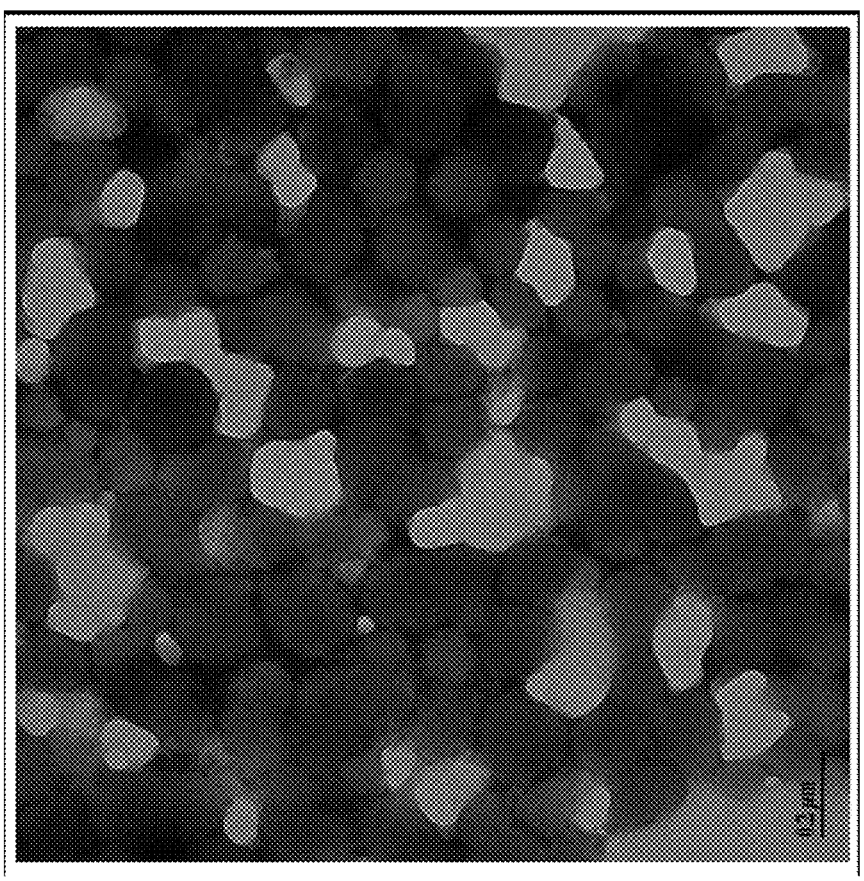

FIG. 9 is a negative staining TEM micrograph of a whey protein micelles dispersion obtained at 4% protein content.

Figure 10:
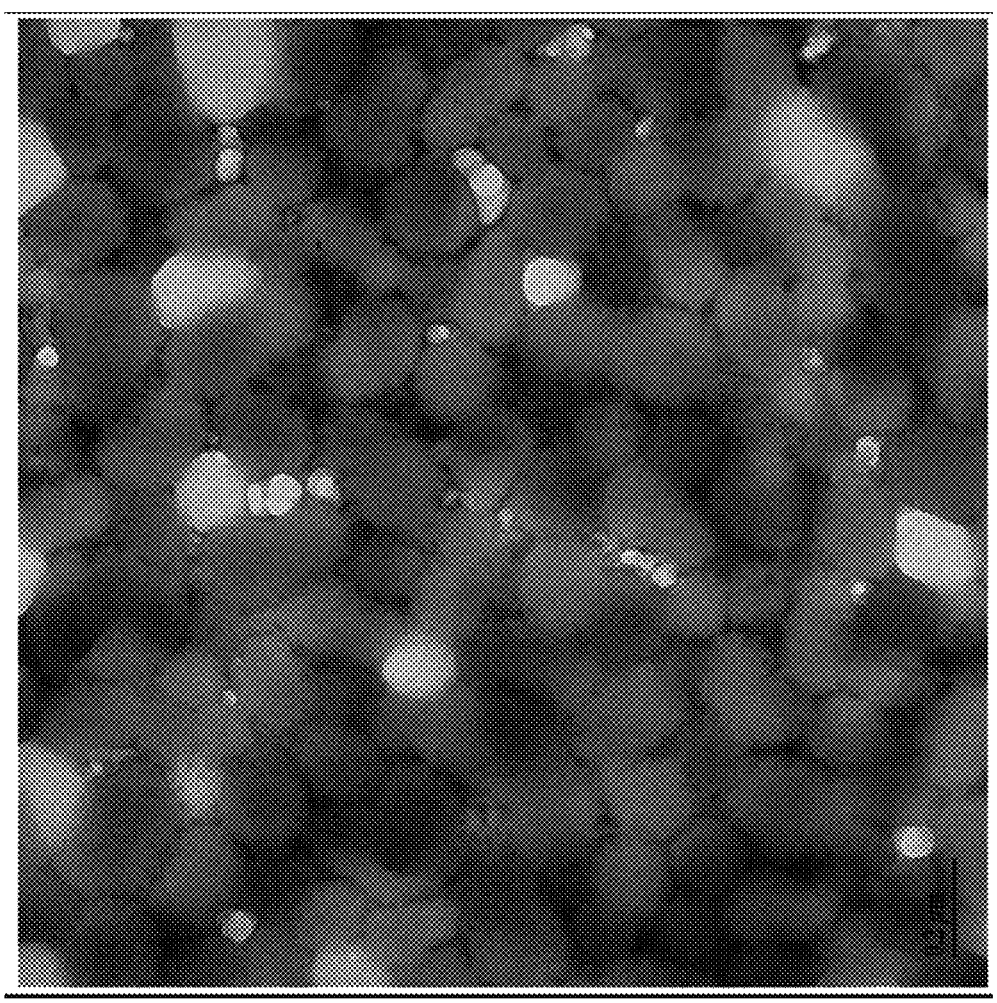

FIG. 10 is a negative staining TEM micrograph of a whey protein micelle dispersion obtained at 20% protein content after microfiltration.

Figure 11:
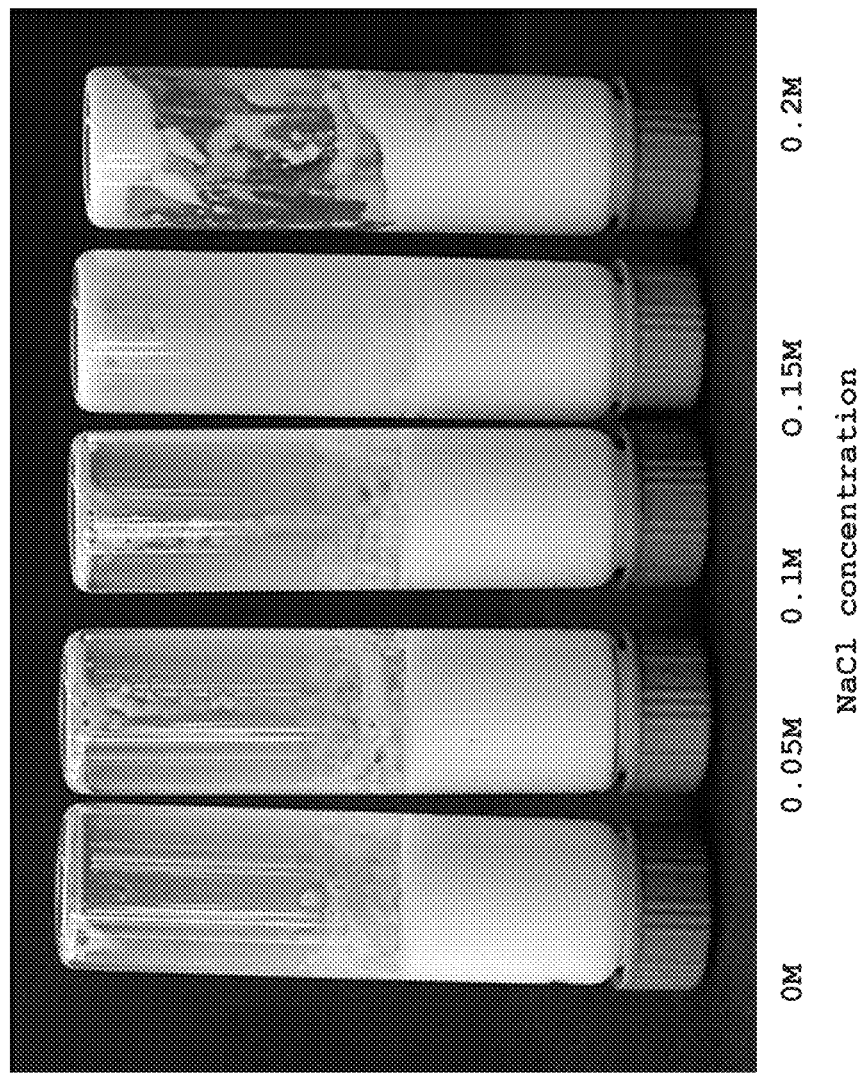

FIG. 11 shows the heat stability of a whey protein micelle dispersion obtained at 10% protein content after microfiltration at pH 7.0 in presence of NaCl after heating at 85° C. for 15 min.

Figure 12:
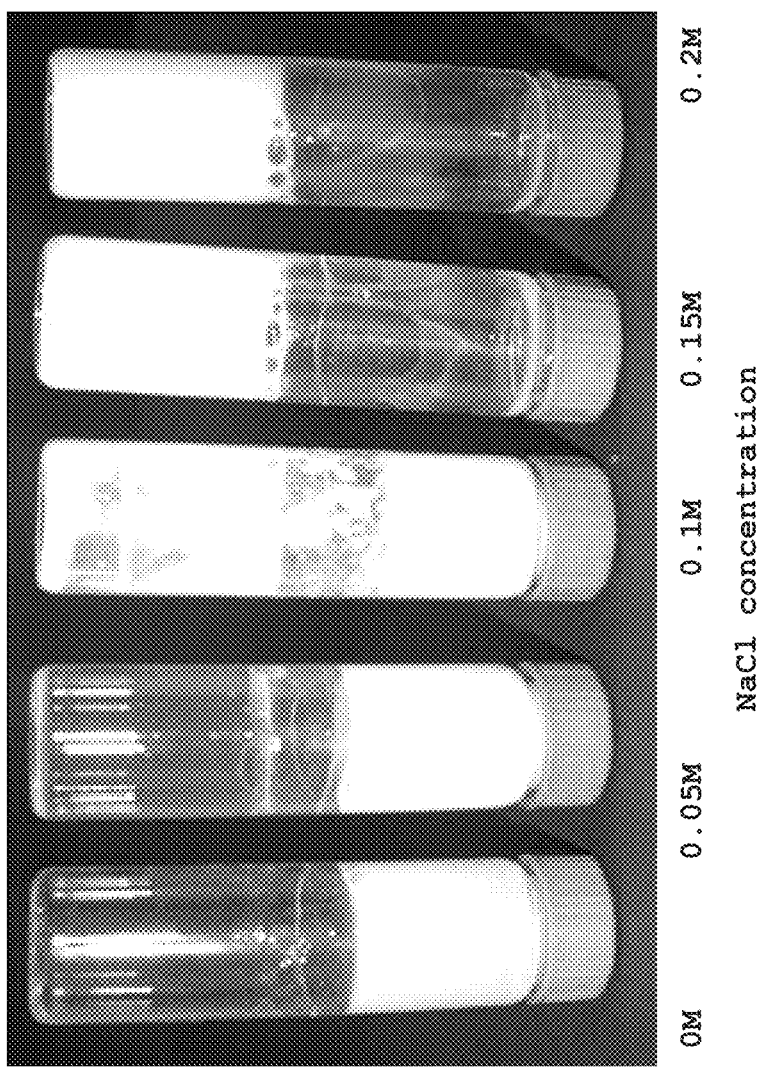

FIG. 12 shows the heat stability of a whey protein dispersion obtained at 4% protein content at pH 7.0 in presence of NaCl after heating at 85° C. for 15 min.

Figure 13:
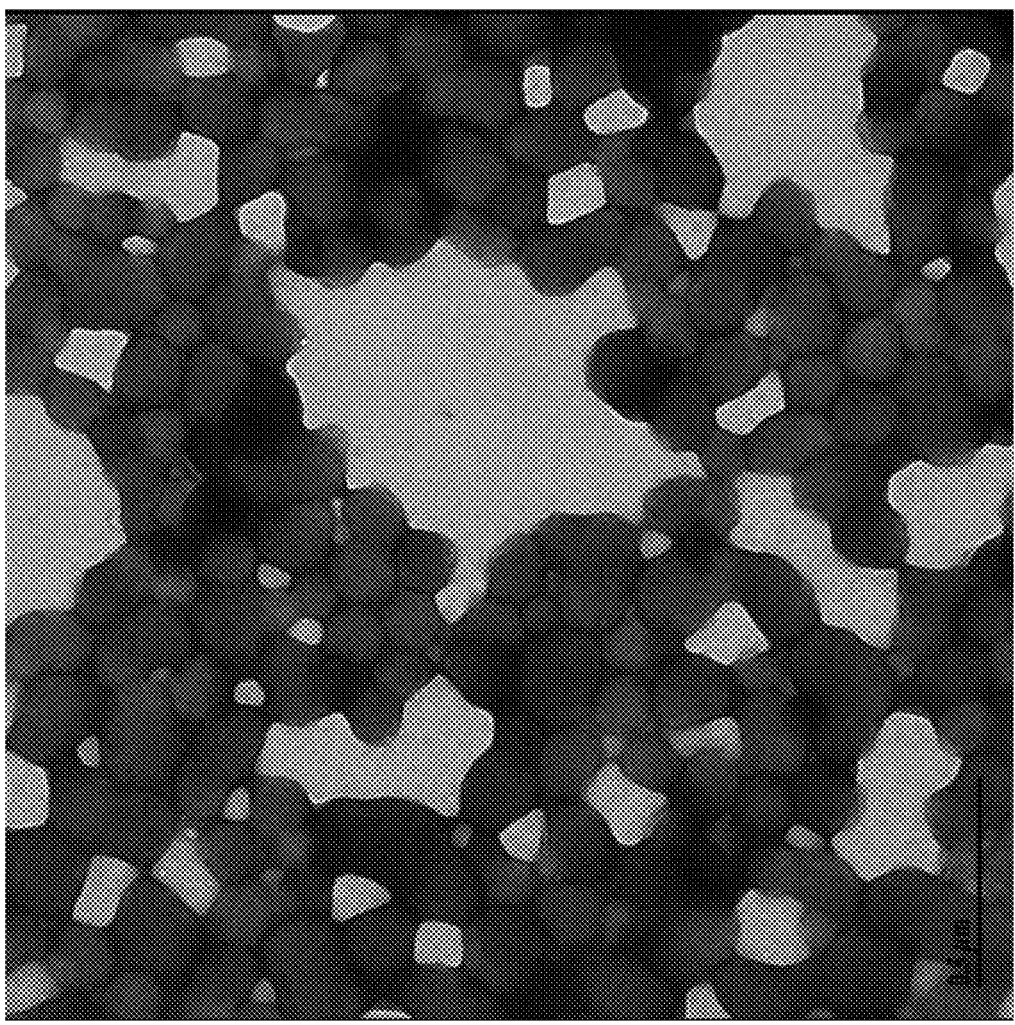

FIG. 13 is a negative staining TEM micrograph from a 4% whey protein micelles dispersion based on a pure whey protein micelle spray dried powder after dispersion at 50° C. in deionised water.

Figure 14:
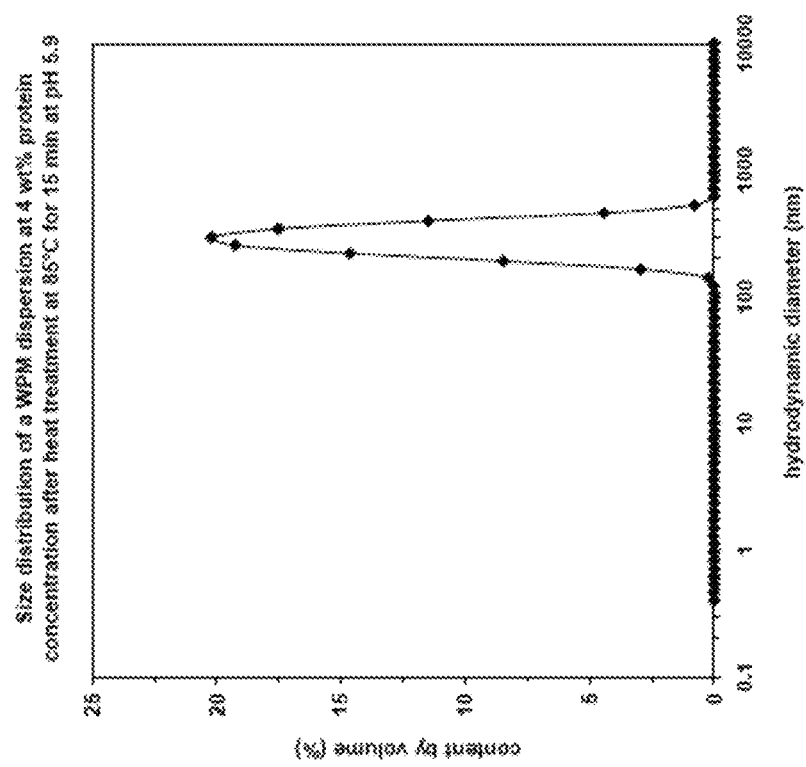

FIG. 14 is a graph showing the size distribution of micelles obtained by the process of the invention using a 4t% Prolacta 90 whey protein isolate treated at pH 5.9.

Figure 15:
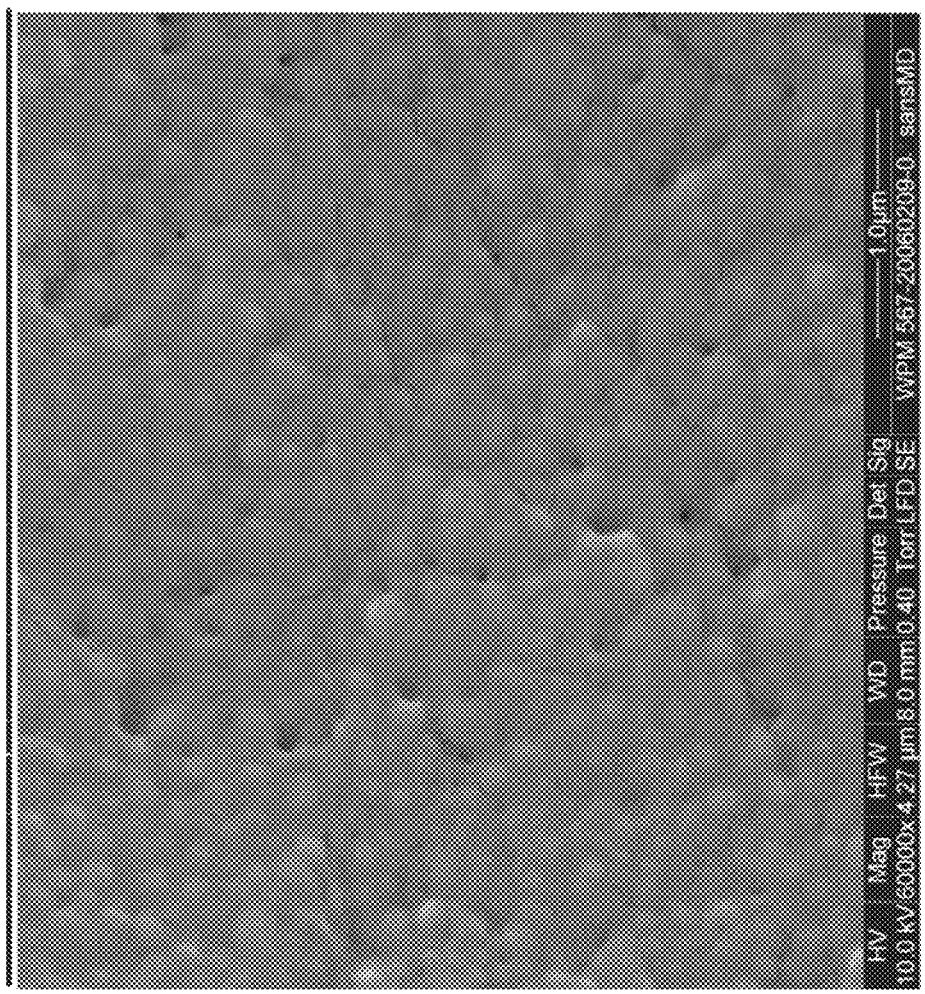
Figure 6:
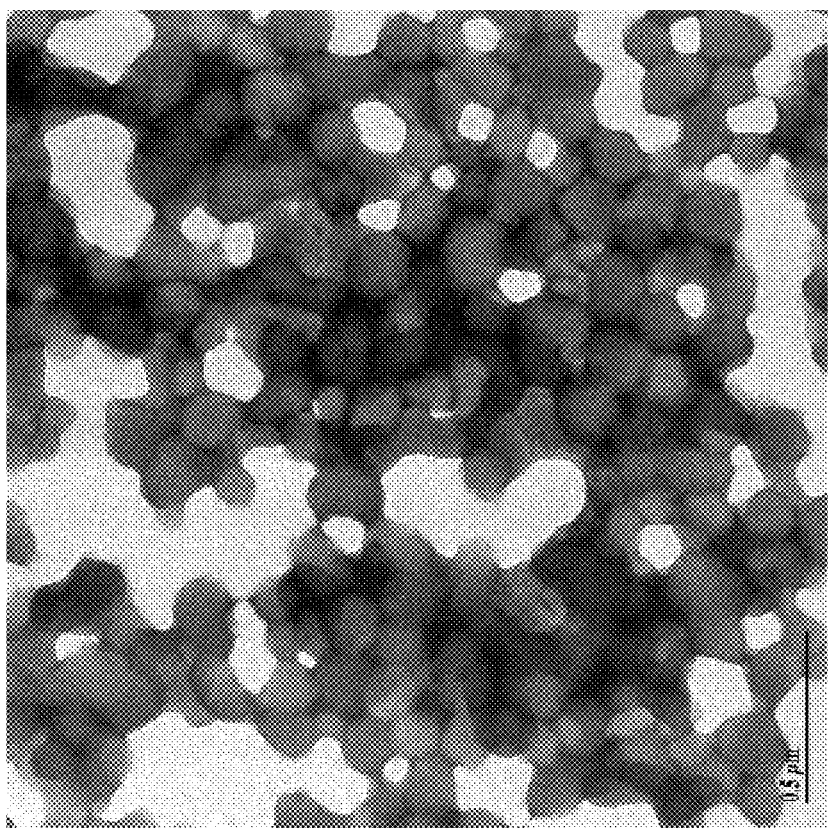

FIG. 15 is a SEM micrograph showing the internal structure after cutting of a spray-dried powder granule that is presented on FIG. 8.

FIG. 16 is a negative staining TEM micrograph of a 4% whey protein micelles dispersion based on a pure freeze dried whey protein micelle powder after at room temperature in deionised water. Scale bar is 0.5 micrometer.

Figure 17:
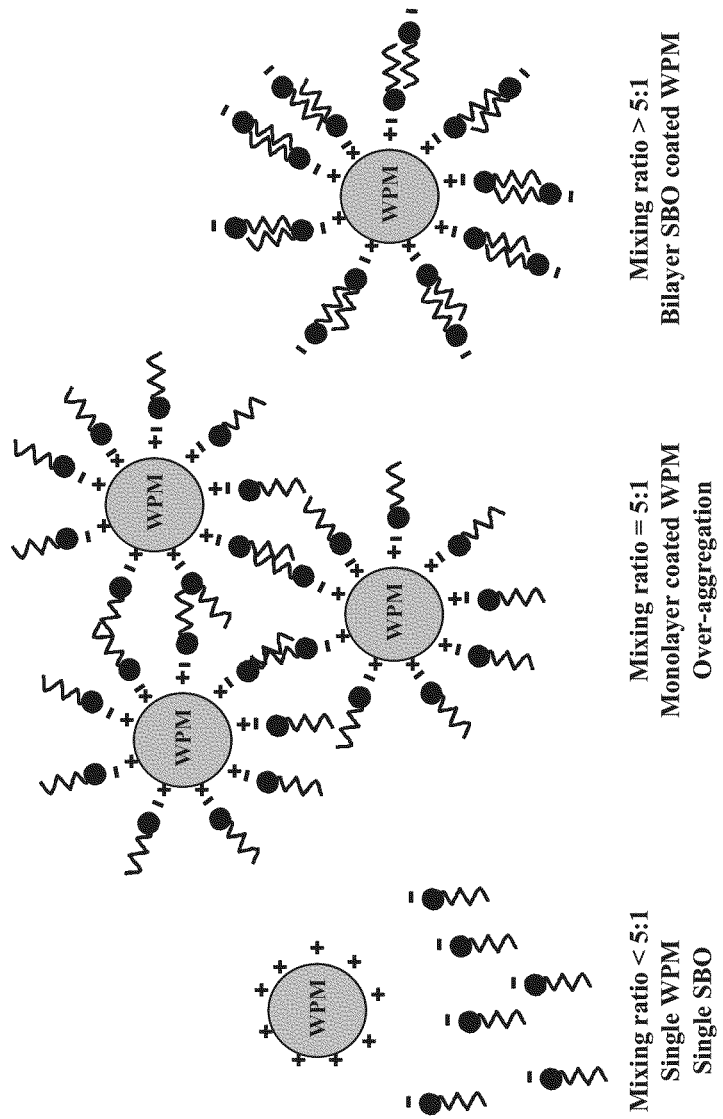

FIG. 17 is a schematic view of the WPM coating by SBO (sulphated butyl oleate) upon increasing the mixing ratio at pH 3.0. Grey circle: WPM with positive surface charges. Black head+tail: negatively charged head and hydrophobic tail from SBO.

Figure 18:

FIG. 18 is a photograph of a whey protein micelle concentrate at 20% obtained after evaporation in which 4% NaCl is added.

Figure 19:
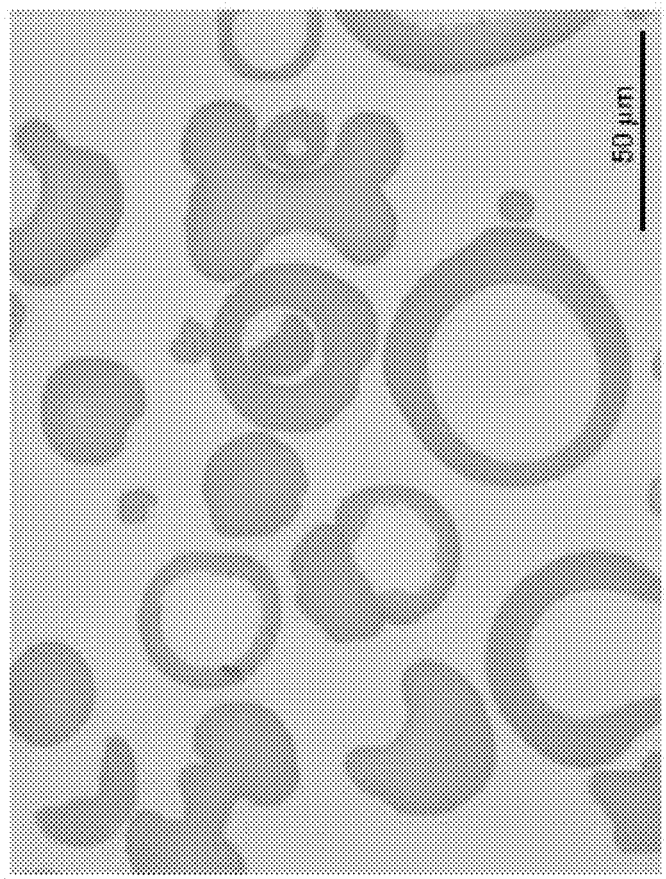

FIG. 19 is a bright field light microscopy micrograph of whey protein micelle powder semi-thin section after toluidine blue staining. Scale bar is 50 microns.

Figure 20:
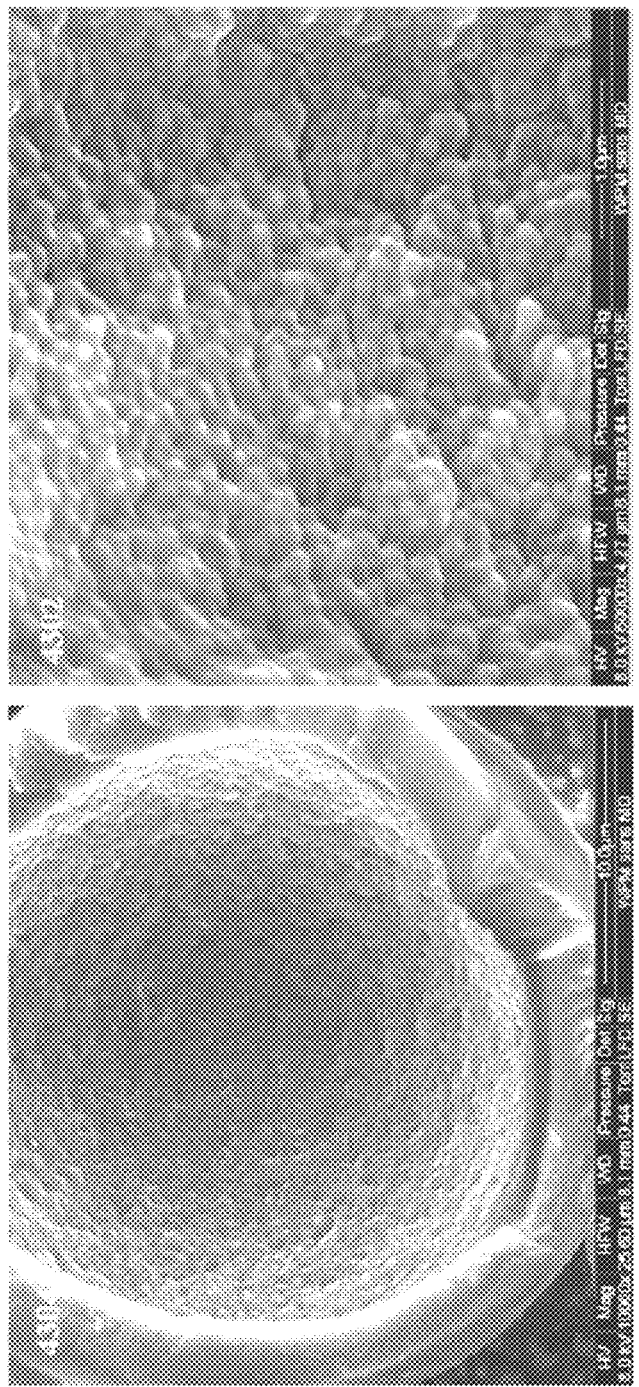

FIG. 20 is a SEM micrograph of the hollow whey protein micelle powder particle after cutting. Left: internal structure. Right: Detail of the whey protein micelle composing the powder particle matrix. Scale bars are 10 and 1 micron respectively.

DETAILED DESCRIPTION OF THE INVENTION

According to the present invention, proteins such as whey protein micelles or aggregates thereof may be used as abrasive medium.

Whey protein micelles which can be used in the context of the present invention are represented in FIG. 7, wherein the whey proteins are arranged in such a way that the hydrophilic parts of the proteins are oriented towards the outer part of the agglomerate and the hydrophobic parts of the proteins are oriented towards the inner "core" of the micelle. This energetically favourable configuration offers good stability to these structures in a hydrophilic environment.

The specific micelle structure can be seen from the figures, in particular FIGS. 3, 9, 10 and 13, wherein the micelles used in the present invention consist essentially of spherical agglomerates of denatured whey protein. The micelles of the present invention are particularly characterised by their regular, spherical shape.

Whey protein micelles may be produced by a process of firstly adjusting the pH and/or ionic strength of a native whey protein aqueous solution, and then subjecting said solution to heat. Such process is described in more detail further herein.

The whey protein micelles thus produced have a dual character (hydrophilic and hydrophobic). Indeed, the arrangement of the denatured whey proteins into a micelle structure seems to allow interaction with a hydrophobic phase, e.g. a fat droplet or air, and a hydrophilic phase. The whey protein micelles therefore have perfect emulsifying and foaming properties.

Furthermore, the whey protein micelles used in the present invention are produced in such a way that they have an extremely sharp size distribution (see FIG. 14), such that more than 80% of the micelles produced will have a size smaller than 1 micron. Preferably the whey protein micelles used in the present invention will have a size between 100 nm and 900 nm, more preferably between 100-770 nm, most preferably between 200 and 400 nm.

The mean diameter of the micelles can be determined using Transmission Electron Microscopy (TEM). In order to do so, the liquid micelle samples are encapsulated in agar gel tubes. Fixation is achieved by immersion in a solution of 2.5% glutaraldehyde in 0.1M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples are embedded in Spurr resin (Spurr/ethanol 1:1, 2:1, 100%). After polymerization of the resin (70° C., 48 hours), semi-thin and ultra-thin sections are cut with a Leica ultracut UCT ultra-microtome. Ultra-thin sections, stained with aqueous uranyl-acetate and lead citrate, are then examined by transmission electron microscopy (Philips CM12, 80 kV).

Without wishing to be bound by theory, it is thought that during micelle formation, the micelles reach a "maximum" size, due to the overall electrostatic charge of the micelle repelling any additional protein molecule, such that the micelle cannot grow in size any longer. This accounts for the sharp size distribution observed (cf. FIG. 14).

The whey protein micelles used in the present invention can be produced from any commercially available whey protein isolates or concentrates, i.e. whey protein obtained by any process for the preparation of whey protein known in the art, as well as whey protein fractions prepared therefrom or proteins such as β-lactoglobulin (BLG), α-lactalbumin and serum albumin. In particular, sweet whey obtained as a by-product in cheese manufacture, acid whey obtained as by-product in acid casein manufacture, native whey obtained by milk microfiltration or rennet whey obtained as a by-product in rennet casein manufacture may all be used as the whey protein source. The whey protein may be from a single source or from mixtures of any sources. It is preferable that the whey protein does not undergo any hydrolysis step prior to micelle formation. Thus, the whey protein is not subjected to any enzymatic treatment prior to micellisation. According to the invention, it is important that the whey protein be used in the micelle formation process and not hydrolysates thereof.

Whey isolates used to produce the whey protein micelles used in the present invention are not restricted to those of bovine origin, but include whey isolates from all mammalian animal species, such as from sheep, goats, horses, and camels. Also, the whey preparations may be mineralised, demineralised or slightly mineralised. By "slightly mineralized" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no specific mineral enrichment.

For the manufacture of whey protein micelles, whey proteins may be present in an aqueous solution in an amount of 0.1 wt. % to 12 wt. %, preferably in an amount of 0.1 wt. % to 8 wt. %, more preferably in an amount of 0.2 wt. % to 7 wt. %, even more preferably in an amount of 0.5 wt. % to 6 wt. %, most preferably in an amount of 1 wt. % to 4 wt. % on the basis of the total weight of the solution.

The aqueous solution of the whey protein preparation as present before the micellisation step may also comprise additional compounds, such as by-products of the respective whey production processes, other proteins, gums, carrageenans or carbohydrates. The solution may also contain other food ingredients (fat, carbohydrates, plant extracts, etc). The amount of such additional compounds generally doesn't exceed 50 wt. %, preferably 20%, and more preferably does not exceed 10 wt. % of the total weight of the solution.

The whey protein, as well as the fractions and/or the main proteins thereof may be used in purified form or likewise in form of a crude product. The content of divalent cations in the whey protein for the preparation of the whey protein micelles may be less than 2.5%, preferably less than 0.2%. Most preferably the whey proteins are completely demineralised.

Figure 1:
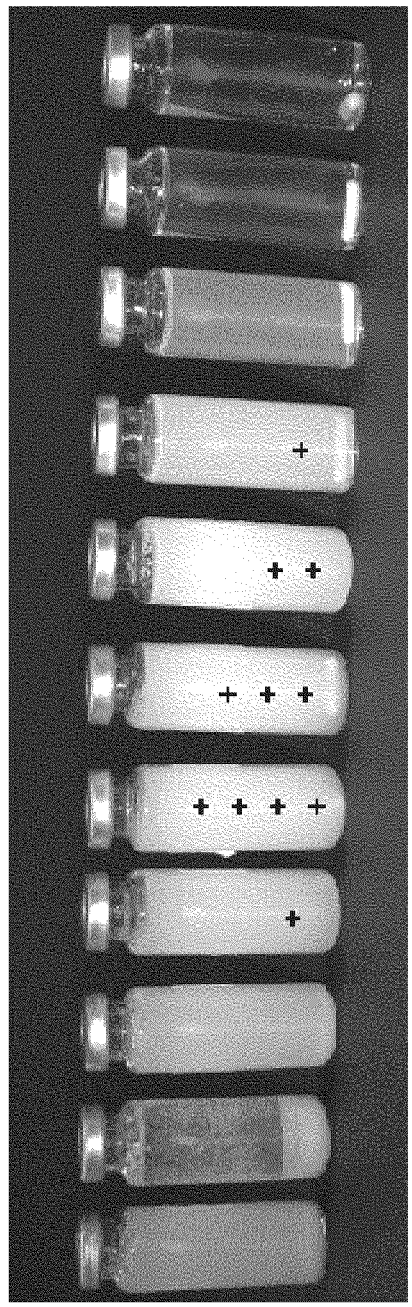
FIG. 1 shows the result of an experiment demonstrating the effect of pH and heat treatment on the micellisation of β-lactoglobulin.

PH values and ionic strength are important factors in the manufacture of whey protein micelles. Thus, for extensively dialyzed samples which are virtually devoid or depleted of free cations such as Ca, K, Na, Mg, when performing the heat treatment during a time period of 10 s to 2 hours at a pH below 5.4, curd is obtained, while at a pH exceeding 6.8, soluble whey protein results (see FIG. 1). Thus, only in this rather narrow pH window will whey proteins micelles having a diameter of less than 1 μm be obtained. These micelles will have an overall negative charge. The same micelle form can also be obtained symmetrically below the isoelectrical pH, i.e from 3.5 to 5.0, more preferably 3.8 to 4.5 resulting in micelles being positively charged (see FIG. 6).

Thus, in order to obtain positively charged micelles, micellisation of whey proteins may be done in a salt free solution at a pH value adjusted between 3.8 and 4.5 depending on the mineral content of the protein source.

Alternatively, in order to obtain negatively charged micelles, the pH may be adjusted to a range of from 6.3 to 9.0, for a content in divalent cations comprised between 0.2% and 2.5% in whey protein powder.

More specifically, to obtain negatively charged micelles, the pH is adjusted to a range of from 5.6 to 6.4, or even from 5.8 to 6.0 for a low divalent cation content (e.g. less than 0.2% of the initial whey protein powder). The pH may be increased up to 8.4 depending on the mineral content of whey protein source (concentrate or isolate). In particular, the pH may be between 7.5 to 8.4, preferably 7.6 to 8.0 to obtain negatively charged micelles in the presence of large amounts of free minerals and the pH may be between 6.4 to 7.4, preferably 6.6 to 7.2 to obtain negatively charged micelles in the presence of moderate amounts of free minerals. As a general rule, the higher the calcium and/or magnesium content of the initial whey protein powder, the higher the pH of micellisation.

The conditions of formation of the whey protein micelles, may be standardised by demineralising—by any of the known demineralisation techniques (dialysis, ultrafiltration, reverse osmosis, ion exchange chromatography . . . )—any source of liquid native whey proteins with a protein concentration ranging from that of sweet whey, microfiltration permeate of milk or acid whey (0.9% protein content) to that of a concentrate at 30% protein content. The dialysis can be done against water (distilled, deionised or soft), but as this will only allow removal of the ions weakly bound to the whey proteins, it is usual to dialyse against an acid at pH below 4.0 (organic or inorganic) to better control the ionic composition of the whey proteins. By doing so, the pH of whey protein micelle formation will be below pH 7.0, usually comprised between 5.8 to 6.6.

Prior to heating the whey protein aqueous solution, the pH is generally adjusted by the addition of acid such as e.g. hydrochloric acid, phosphoric acid, acetic acid, citric acid, gluconic acid or lactic acid. When the mineral content is high, the pH is generally adjusted by the addition of alkaline solution such as sodium hydroxide, potassium hydroxide or ammonium hydroxide.

Figure 4:
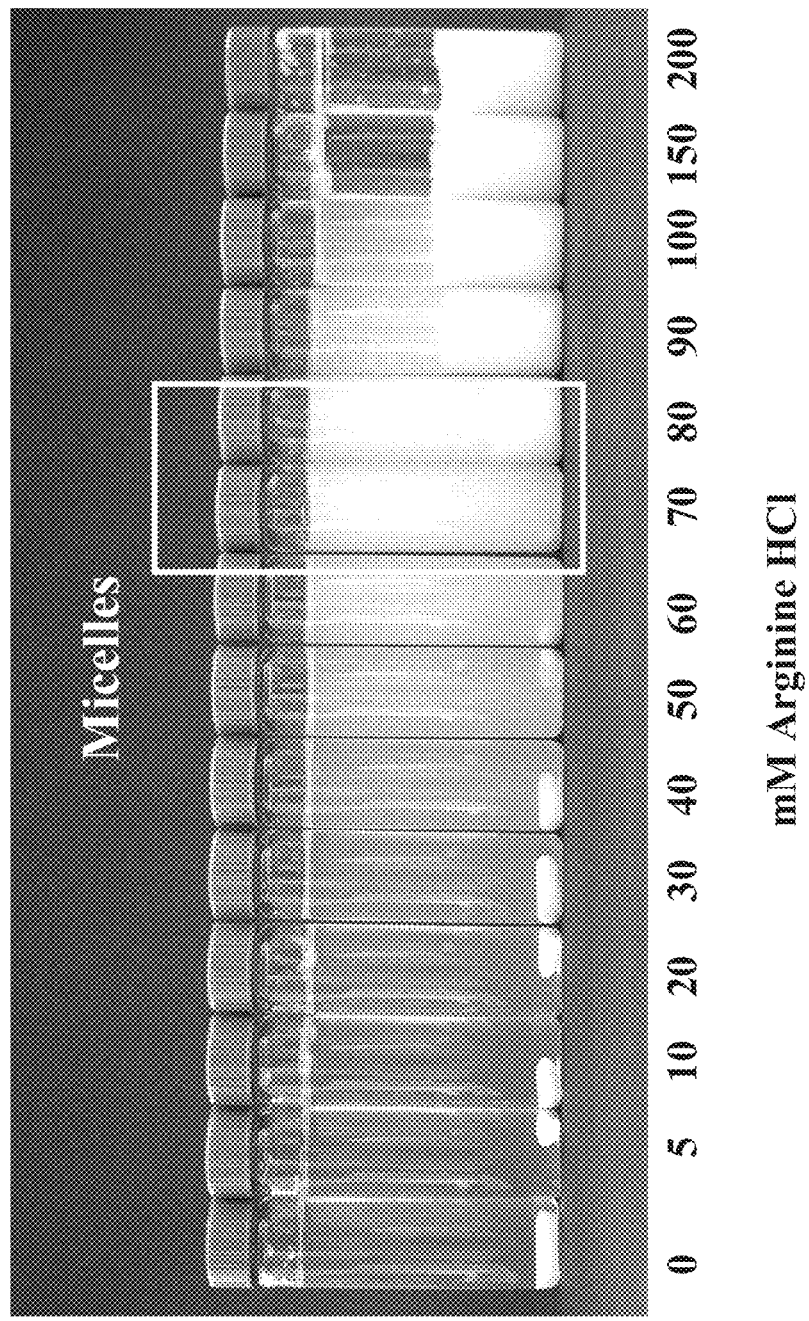
FIG. 4 shows the result of an experiment evaluating the impact of the ionic strength (Arginine HCl) on the formation of protein micelles at constant pH of 7.0.

Alternatively, if no pH adjustment step is desired, it is possible to adjust the ionic strength of the whey protein preparation while keeping the pH constant. Then, ionic strength may be adjusted by organic or inorganic ions in such a way that allows micellisation at a constant pH value of 7. FIG. 4 illustrates micelles being formed at a constant pH value of 7.0 while the ionic strength is varied by the addition of 70-80 mM of arginine HCl.

A buffer may be further added to the aqueous solution of whey protein so as to avoid a substantial change of the pH value during heat treatment of the whey protein. In principle, the buffer may be selected from any buffer system, i.e. acetic acid and its salts, such as e.g. sodium acetate or potassium acetate, phosphoric acid and salts thereof, e.g. $NaH_2PO_4$, $Na_2HPO_4$, $KH_2PO_4$, $K_2HPO_4$, or citric acid and salts thereof etc.

Adjusting the pH and/or the ionic strength of the aqueous solution prior to heating results in a controlled process yielding micelles having a size between 100nm-900 nm, preferably 100-700 nm, most preferably 200-400 nm. Preferably, the distribution of micelles having dimensions between 100-700 nm is greater than 80% when carrying out the process described herein (see FIG. 14).

In order to obtain regular shape micelles, it is also important, according to the invention, that the whey protein does not undergo any hydrolysation step prior to micelle formation.

After adjusting the pH and/or ionic strength, the starting whey protein aqueous solution is subjected to heat treatment. In this respect, in order to obtain whey protein micelles, it is important to have the temperature in the range of from about 70 to below 95° C., preferably of from about 82 to about 89° C., more preferably of from about 84 to about 87° C., most preferred at about 85° C. It has also been found that, on an industrial scale, it is important that the temperature be preferably less than 95° C., more preferably between 80° C. and 90° C., most preferably about 85° C.

Once the desired temperature has been reached, the solution is kept at this temperature for a minimum of 10 seconds and a maximum of 2 hours. Preferably, the time period during which the aqueous whey protein solution is kept at the desired temperature ranges from 12 to 25 minutes, more preferably from 12 to 20 minutes, or most preferably about 15 minutes.

The heat treatment may also be achieved in a microwave oven or any similar equipment allowing heating by microwaves with a time/quantity ratio of 10 s/10 mL for a 4 wt % protein solution heated in a 1500 W apparatus up to boiling temperature (98° C. at an altitude of 833 m). A continuous process may also be used by addition of 8 or more magnetrons around a glass tube potentially prolonged by a holding tube to increase the time of incubation.

Figure 2:
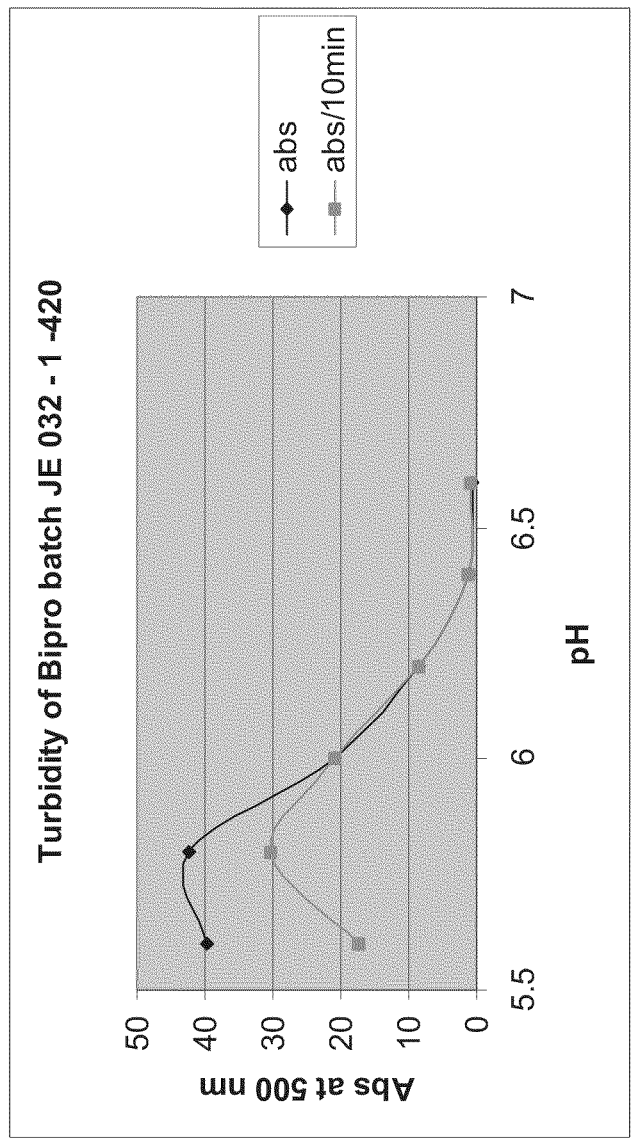
FIG. 2 is showing a mean to determine the pH of micellisation for a commercial preparation (Bipro®, Batch JE032-1-420) using turbidity measurements at 500 nm.

As shown in FIG. 2, turbidity measurements are an indication of micelle formation. The turbidity measured by absorbance at 500 nm is generally at least 3 absorbance units for 1% protein solution but can reach 16 absorbance units when the yield of micellisation is above 80% (see FIG. 2).

To further illustrate the effect of micelle formation from a physicochemical point of view, a 1 wt % dispersion of Bipro® has been heated for 15 minutes at 85° C. at pH 6.0 and 6.8 in MilliQ water. The hydrodynamic diameter of the aggregates obtained after heat treatment was measured by dynamic light scattering. The apparent molecular weight of the aggregates was determined by static light scattering using the so-called Debye plot. The surface hydrophobicity was probed using the hydrophobic ANS probe and the free accessible thiol groups by the DTNB method using cystein as the standard amino acid. Finally, the morphology of the aggregates was studied by negative staining TEM. The results are presented in table 1.

From table 1, it is clear that the whey protein micelles that were formed at pH 6.0 allow protein to decrease its specific ANS surface hydrophobicity by a factor of 2 compared to non-micellised whey protein heated in the same condition, but at pH 6.8. The micelle formation can be also seen on the very high molecular weight of $27 \times 10^6$ g.mol$^{-1}$ compared to $0.64 \times 10^6$ g.mol$^{-1}$ for non-micellised protein, indicating a very condensed state of the matter within the micelle (low amount of water). Interestingly enough, the ζ-potential of the micelles is even more negative than the non-micellised proteins even if the latter have been formed at a more basic pH than the micelles. This is the result of a more hydrophilic surface of the micelles being exposed to the solvent. Finally, one should note that the thiol reactivity of the micelles is much lower than that of the non-micellised protein because of the different pH of heat treatment.

TABLE 1

Physicochemical properties of soluble whey protein aggregates obtained by heat treatment (85° C., 15 min) of a 1 wt % protein dispersion in presence or absence of NaCl.

| pH | hydrodynamic diameter (nm) | molecular weight $M_w$ ($\times 10^{6\,g\cdot mol-1}$) | morphology | ζ-potential (mV) | protein surface hydrophobicity ($\mu g \cdot mmol^{-1}$ ANS) | accessible SH groups (nmol $SH \cdot mg^{-1}$ prot.) |
|---|---|---|---|---|---|---|
| 6.0 | 120.3 ± 9.1 | 27.02 ± 8.09 | Spherical micelles | −31.8 ± 0.8 | 105.4 | 3.5 ± 0.4 |
| 6.8 | 56.2 ± 4.6 | 0.64 ± 0.01 | linear aggregates | −27.9 ± 1.2 | 200.8 | 6.8 ± 0.5 |

The conversion yield of native whey protein to micelles decreases when the initial protein concentration is increased before pH adjustment and heat treatment. For example, when starting with a whey protein isolate Prolacta 90 (lot 673 from Lactalis), the yield of formation of whey protein micelles drops from 85% (when starting with 4% proteins) to 50% (when starting with 12% of proteins). In order to maximize the formation of whey protein micelles (>85% of the initial protein content), it is better to start with an aqueous whey protein solution having a protein concentration below 12%, preferably below 4%. Depending on the intended final application, the protein concentration may be adjusted before heat treatment to manage the optimal whey protein micelles yield.

Depending on the desired application, the yield of micelles before concentration is of at least 50%, preferably at least 80% and the residual soluble aggregates or soluble protein content is preferably below 20%. The average micelle size is characterised by a polydispersity index below 0.200. It has been observed that whey protein micelles could form aggregates around pH 4.5, with however no sign of macroscopic phase separation after at least 12 hours at 4° C.

The purity of whey protein micelles can be obtained by determining the amount of residual soluble proteins after production. Micelles are eliminated by centrifugation at 20° C. and 26900 g for 15 min. The supernatant is used to determine the protein amount in quartz cuvettes at 280 nm (1 cm light pathlength). Values are expressed as a percentage of the initial value before heat treatment.

Proportion of micelles=(Amount of initial proteins−amount of soluble proteins)/Amount of initial proteins By using the process described herein, the whey protein micelles are not submitted to any mechanical stress leading to reduction of the particle size during formation, contrary to conventional processes. The method induces spontaneous micellisation of whey proteins during heat treatment in the absence of shearing.

The micelles may be obtained as a suspension or a dispersion in a liquid and may have a size ranging from 100 to 900 nm, preferably from 100-770 nm, most preferably 200-400 nm.

The micelles obtainable by the process described herein are extremely stable, insoluble structures which may be used as abrasive medium according to the present invention.

Said micelles may be used as such in the present invention or may undergo further processing, such as concentration, spray-drying etc. while retaining their abrading properties.

Indeed, further concentration of the micelles dispersion obtainable after heat treatment may be carried out by evaporation, centrifugation, sedimentation, microfiltration and/or ultrafiltration for instance.

The enrichment of the whey protein micelles to produce concentrates thereof offers the advantage that protein-enriched products may be obtained at concentration previously not attainable. Thus, the micelle suspension may be concentrated to a protein content of greater than 4%, preferably greater than 10%, more preferably greater than 20%.

Evaporation may be performed by feeding the micelles dispersion to an evaporator under vacuum, having a temperature between 50° C. and 85° C. The resulting product will generally have the aspect of a gel or a cream as shown in FIG. 18. Such micelle product may be used as such as an abrasive medium or as a cosmetic agent, or in the cosmetic compositions of the present invention. Furthermore, the 20% protein concentrate of whey protein micelles obtainable by evaporation may be texturised in a spreadable texture by acidification using lactic acid.

Centrifugation may be carried out with high acceleration rate (more than 2000 g) or low acceleration rate (less than 500 g) after acidification of the whey protein micelle dispersion at a pH lower than 5, preferably 4.5.

Spontaneous sedimentation may also be carried out on the whey protein micelle dispersion by acidification. Preferably, the pH will be 4.5 and the sedimentation time is more than 12 hours.

Alternatively, concentration of the whey protein micelles used in the present invention may be achieved by microfiltration of the micelles dispersion. This enriching technique not only enables to concentrate whey protein micelles by removing the solvent but also enables the removal of non-micellised protein (such as native proteins or soluble aggregates). Thus, the final product essentially only consists of micelles (as checked by Transmission Electron Microscopy—cf. FIGS. 9 and 10). In this case, the concentration factor that is possible to achieve is obtained after the initial flow rate of permeate through the membrane has dropped to 20% of its initial value. This allows to obtain micelles in a concentration greater than 80%.

Further processing of whey protein micelles may be carried out on the micelle dispersion obtainable using the process described herein.

For instance, the whey protein micelles may be coated with an emulsifier such as phospholipids, for example, or other coating agents such as a protein, a peptide, a protein hydrolysate or a gum such as acacia gum in order to modulate the functionality of the whey protein micelles. When a protein is used as a coating agent, it may be selected from any proteins having an isoelectric point significantly higher or lower than whey protein. These are, for example, protamine, lactoferrin and some rice proteins. When a protein hydrolysate is used as coating agent, it is preferably a hydrolysate from proteins such as protamine, lactoferrin, rice, casein, whey, wheat, soy protein or mixtures thereof. Preferably, the coating is an emulsifier selected from sulphated butyl oleate, diacetyltartaric acid esters of mono- and diglycerides, citric acid esters of monoglycerides, stearoyl lactylates and mixtures thereof. FIG. 17 is a schematic representation of such coating with sulphated butyl oleate. Furthermore, co-spraydrying, as described further herein, may also result in a coating of the whey protein micelles.

Further processing such as drying e.g. spray-drying, freeze-drying, roller drying etc. may also be carried out on the whey protein micelles. Thus, the whey protein concentrate may be spray-dried with or without addition of further ingredients and may be used as a delivery system or a building block to be used in a wide range of processes, e.g. consumables production, cosmetic applications etc.

FIG. 8 shows a powder obtained by spray-drying without addition of any further ingredients, having an average particle diameter size greater than 1 micron due to the micelle aggregation occurring during spray-drying. A typical average volume median diameter ($D_{43}$) of the whey protein micelles powders is between 45 and 55 microns, preferably 51 microns. The surface median diameter ($D_{32}$) of these powders is preferably between 3 and 4 microns, more preferably it is 3.8 microns.

The moisture content of the powders obtained after spray-drying is preferably less than 10%, more preferably less than 4%.

Such a whey protein micelle powder is considered as "pure" as it comprises at least 90% whey protein from which at least 80% are in the micellar form.

Furthermore, the "pure" whey protein micelles powder have a high binding capacity for solvents such as water, glycerol, ethanol, oil, organic solvents etc. The binding capacity of the powders to water is at least 50%, preferably at least 90%, most preferably at least 100%.

For solvents such as glycerol and ethanol, the binding capacity is of at least 50%. This property of the whey protein micelle powders allows these to be sprayed or filled with further active agents selected from the group of peptides, plant extracts, protein hydrolysates, bioactives, vitamins, minerals, pharmaceuticals, cosmetic components etc. and mixtures thereof.

The active agents may be included in the powder in an amount of 0.1-50%. Thus, the powder may act as a carrier for those functional ingredients.

Additional ingredients which may be mixed to the whey protein micelles or a concentrate thereof prior to spray-drying comprise soluble or non-soluble salts, peptides, protein hydrolysates, pigments, fats, emulsifiers, aroma, plant extracts, ligands or bioactives (minerals, vitamins, drugs . . . ), milk, milk proteins, skimmed milk powder, micellar casein, caseinate, vegetal protein, amino acids, polyphenols and any mixtures thereof. The resulting mixed whey protein micelle powders comprise whey protein micelles and additional ingredients in a weight ratio ranging from 1:1 to 1:1000. This results in agglomerates further comprising these additional ingredients, such that they may be used according to the present invention as abrasive media which exhibit further functional properties and health benefits, depending on the additional ingredient used. The mixed powder may therefore act as a carrier for bioactive agents for instance.

The whey protein micelle powders obtained by the present invention are characterised by an internal structure composed mainly of hollow spheres but also of collapsed spheres (cf. FIG. 19). The hollow spheres structure can be easily explained by the formation of the vapour droplet within the WPM concentrate droplet during the spray drying. As the vapour droplet left the WPM droplet due to a temperature above 100° C., a hollow sphere remained. The "bone-shape" is due to a combination of the water evaporation from droplet and the external pressure within the droplet.

The internal structure of the spherical hollow spheres was investigated by SEM after sectioning the particle close to its diameter (FIG. 20, left). The wall thickness of the particle was around 5 μm and seemed very smooth, whereas the inner structure had a more grainy appearance. Increased magnification showed that this graininess was in fact due to the presence of the initial WPM that were fused to form the inner matrix of the powder particle. Interestingly, the spherical shape of the micelles was kept during spray drying as well the homogeneous particle size distribution (FIG. 20, right).

Thus, on a microscopic basis, whey protein micelle powders are characterised by a unique granule morphology of hollow or collapsed spheres containing intact and individualised whey protein micelles.

Whey protein micelle powders are characterised by a very high flowability, which offers the advantages of easy usability and transferability. The angle of repose of these powders is preferably below 35°, more preferably below 30°. Such a low angle of repose allows the powders to be used as flowing agents in cosmetic applications, for instance.

These powders may also be used according to the present invention, for instance as abrasive medium, as cosmetic agent or in the manufacture of a cosmetic composition.

The size of the powder particles, i.e. of the whey protein micelle aggregates and the size of the whey protein micelles themselves present the advantage that the whey protein micelles or aggregates thereof are barely perceptible and will act as an abrasive agent without irritating the skin, when used in topical applications.

An important feature of whey protein micelles, regardless of their form (concentrate, suspension, dried powder etc.) is that the basic micelle structure of the whey proteins is conserved. FIG. 15 shows a whey protein powder grain which has been sectioned, and whereby the individual whey protein micelles are observable. Furthermore, the micelle structure can be easily reconstituted in solvents. For instance, it has been shown that the powders obtained from whey protein micelle concentrate can be easily redispersed in water at room temperature or at 50° C. The size and structure of the whey protein micelles are fully conserved compared to the initial concentrate. For example, in FIG. 13, the whey protein concentrate that was spray-dried at 20% protein concentration has been redispersed in deionised water at 50° C. at a protein concentration of 50%. The structure of the micelles has been probed by TEM and can be compared to FIG. 10. A similar shape of micelles was obtained. The diameter of the micelles was found to be 315 nm by dynamic light scattering with a polydispersity index of 0.2. FIG. 16 also shows dispersion of a freeze-dried whey protein micelle powder, wherein the micelles are reconstituted.

The fact that the whey protein micelles and only a minor aggregate fraction were observed in solution after reconstitution of the spray-dried or freeze-dried powder confirms that whey protein micelles are physically stable regarding spray-drying, freeze-drying etc.

It is also interesting to note that the concentrate, if adjusted to a protein content of 10% has the ability to withstand a subsequent heat treatment at 85° C. for 15 min at pH 7.0 in presence for example of up to 0.15 M of sodium chloride, as shown in FIG. 11. As a matter of comparison, a native whey protein dispersion (Prolacta90, lot 500658 from Lactalis) forms a gel in the presence of 0.1 M of sodium chloride at a protein concentration of 4% (cf. FIG. 12).

The high stability of the micelle structure is also preserved during the concentration step. This offers the advantage that the abrasive properties imparted by the micelle structure will not be lost during the production, storage etc. of a cosmetic composition according to the present invention.

According to the present invention, whey protein micelles or aggregates thereof may be used as abrasive medium. Aggregates of whey protein micelles may be in the form of spray-dried or freeze-dried powders. They may comprise additional ingredients selected from the group of soluble or non-soluble salts, pigments, fats, emulsifiers, aroma, plant extracts, ligands or bioactives (minerals, vitamins, drugs . . . ) and any mixtures thereof.

According to the present invention, whey protein micelles or said aggregates thereof may be used as cosmetic agents or for the manufacture of a cosmetic composition.

They may be combined with further active agents selected from the group of peptides, plant extracts, protein hydrolysates, bioactives, vitamins, minerals, pharmaceuticals, cosmetic components and mixtures thereof.

Preferably the whey protein micelles or aggregates thereof are contained in the composition in an amount of at least 1%, preferably more than 5%, more preferably more than 10%, even more preferably greater than 20%, most preferably up to 50%.

The whey protein micelles may be present in form of a liquid dispersion, a suspension, a gel, a cream or a powder. Preferably, the concentration of whey protein in said liquid dispersion, suspension, gel, cream or powder is more than 4%, preferably more than 10%.

The whey protein micelles used in the present invention may have an average size in the range of 100 nm to 900 nm, preferably in the range of 100-770 nm, more preferably in the range of 200-400 nm.

On the other hand, the whey protein micelles aggregates used in the present invention may have an average size of more than 1 μm.

Said whey protein micelles or aggregates thereof may be used in the manufacture of shampoo, shower gels etc.

They may also be used in topical applications whereby the whey protein micelles are in the form of a liquid dispersion, a suspension, a cream, a gel or a powder.

Said whey protein micelles may be incorporated into a cosmetic composition for topical application.

According to an embodiment, the invention provides a method for the abrasion of skin particles, comprising the step of applying whey protein micelles to a skin. The whey protein micelles may be in the form of a liquid dispersion, a suspension, a cream, a gel or a powder or may be incorporated into a composition prior to application.

The compositions of the present invention may comprise micelles in an amount of at least 1%, preferably more than 5%, more preferably more than 10%, even more preferably more than 20%, most preferably up to 50%.

Preferably, the concentration of whey protein in the composition is more than 1%, preferably greater than 10%, more preferably greater than 20%, most preferably greater than 50%.

The composition may be in the form of a solution, a cream, a gel, a paste, a foam, a spray etc.

According to an embodiment, the composition is a hair care product, such as a shampoo. It may also be a shower gel or body and/or hair shampoo.

The present invention also provides a process for the manufacture of a cosmetic composition comprising the steps of:
  a. Producing whey protein micelles or aggregates thereof and
  b. Incorporating said micelles or aggregates thereof into a composition.

The whey protein micelles or aggregates thereof and compositions obtained by the process of the present invention are such as those described above.

The abrasive nature of the whey protein micelles allows these to be used in a method for the abrasion of skin particles according to the present invention. This may be carried out by topical application of the whey protein micelles in the form of a suspension, a dispersion, a cream, a gel or a powder, which may be used as such or in combination with further active agents. Such active agents are selected from peptides, plant extracts, protein hydrolysates, bioactives, vitamins, minerals, pharmaceuticals, cosmetic components etc. Furthermore, the whey protein micelles or aggregates thereof may also be incorporated into a composition prior to application. The composition into which the whey protein micelles are incorporated may range from basic cream composition, to elaborate cleansing solutions, soaps, gels, foams, toothpastes, sprays, shampoos etc.

The advantage presented by using whey protein micelles as a cosmetic agent is that not only the abrasive aspect is of interest for removing dead skin cells for example, but the very nature of the micelles allows them to perform other functions. In addition to mechanical abrasive behaviour the whey protein micelles highly negatively charged or positively charged can form electrostatic complexes with oppositely charged impurities from skin to favour their specific elimination. In the same way, the natural hydrophobicity of micelles can help to scavenge lipophilic impurities from skin without never been aggressive and irritative for the skin.

Figure 5:
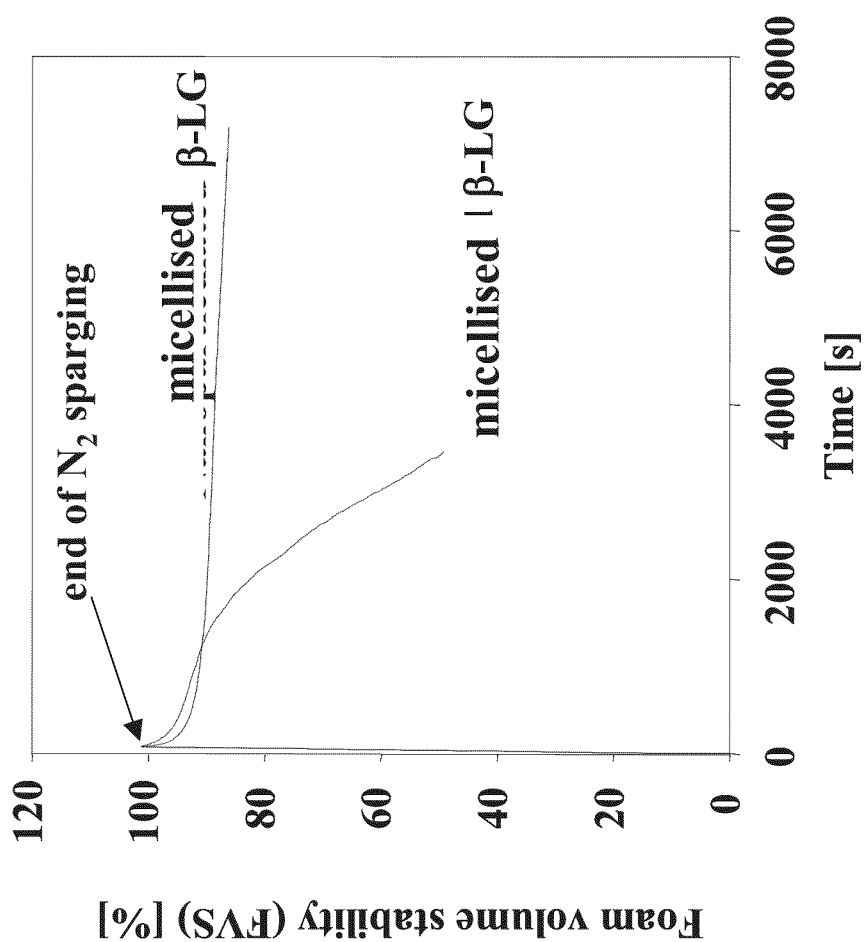
FIG. 5 shows the volume stability (FVS) of foam stabilized by 1 wt. % β-lactoglobulin micelles (Davisco) at pH 7.0 in presence of 60 mM Arginine HCl compared to non-micellised β-lactoglobulin.

Furthermore, whey protein micelles have shown to be ideally suited for use as an emulsifier, whitening agent, fat substitute, substitute for micellar casein or foaming agent, since they are able to stabilize fat and/or air in an aqueous system for prolonged period. The foam stability is shown in FIG. 5 which compares use of non-micellised whey protein versus the whey protein micelles used in the present invention.

Thus, whey protein micelles may be used as an emulsifying agent, for which the material is ideally suited, since it has a neutral taste and no off-flavour is created by the use of such material.

In addition, the present whey protein micelles are still in a condition to serve as whitening agent, so that with one compound several tasks may be fulfilled. Since whey is a material abundantly available, the use thereof reduces the cost of a product requiring an emulsifying, filling, whitening or foaming agent.

Also, in their role as emulsifiers, whey protein micelles may not only be useful as stabilisers of emulsions or foams for example, but they may also help in removing oily residues, providing a full cleansing effect. Furthermore the whey proteins micelles may be used in combination with other active ingredients such as lactoferrin, hydrating, emollient, painkiller, astringent, anti-oxidant antimicrobial, antiviral, anti-inflammatory, drug, antibiotic, substances, acids, rosewater, glycerine etc. They may be used in shampoo as a cleaning agent, a whitening agent or even as a pigmenting agent. They may also be used in shower gels.

Applications for the whey protein micelles in whichever form thus include skin care, mouth care such as toothpaste, mouthwash, gum-cleaning agents etc. and hair care. The whey protein micelles or concentrate thereof may be used as such or diluted depending on the application.

Accordingly, a process for the manufacture of a cosmetic composition is also provided by the present invention, whereby the whey protein micelles are produced according to a process such as described above, and wherein said micelles are further incorporated into a composition.

The composition into which the whey protein micelles are incorporated may range from basic cream composition, to elaborate cleansing solutions, soaps, gels, foams, toothpastes, sprays, shampoos etc. These may also contain further active ingredients such as lactoferrin, hydrating, emollient, painkiller, astringent, anti-oxidant antimicrobial, antiviral, anti-inflammatory, drug, antibiotic, substances, acids, rose distilled water, glycerine, sulfosuccinate, alkyl sulfonate, coco betaine, xantan gum, EDTA, potassium sorbate, Soybean oil, almond oil, propyltrimonium, ceteareth 20, cetyl-alcohol, essential oil ,vegetal oil, hydrogenated castor oil, emulsifier, stabiliser, Paraben-DU, Fragrance, lauryl glucoside, ammonium laureth sulfate, sodium laureth sulphate, butylene glycol, sodium lauroyl sarcosinate, peg-2 sterate, cetearyl alcohol, cleth-12, stearyl alcohol, mieticone, allantoin, disodium EDTA, tetrasodium EDTA, ethylhexyl methoxycinnamate, glycyrrhetinic acid, sodium methylcocyl, taurate, bht, sodium chloride, imidazolidinyl urea, alpha-isomethyl ionone, benzyl salicylate, butylphenyl, methylpropional, hydroxyisohexyl 3-cyclohexene carboxaldehyde, salicylic acid, polyethylene, triethanolamine, xanthan gum, peg-60 hydrogenated castor oil, benzophenone-4, imidazolidinyl urea, decyl glucoside, dimethyl mea, cocamidopropyl betaine, glycolic acid, ppg-2 hydroxyethyl cocamide, glycereth-7, peg-120 methyl glucose dioleate, sodium cocoyl sarcosinate, phenoxyethanol, methylparaben, propylparaben, butylparaben, ethylparaben, isobutylparaben, parfum menthol, citronellol, geraniol, hexyl cinamal, limonene etc.

Typically, the composition will comprise whey protein micelles or aggregates thereof in an amount of at least 1%, 5%, 10%, 20%, up to 50% in powder.

The following examples illustrate the present invention without limiting it thereto.

EXAMPLES

The invention is further defined by reference to the following examples describing in detail the preparation of the micelles of the present invention. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Example 1

Micellisation of β-Lactoglobulin

β-Lactoglobulin (lot JE002-8-922, 13-12-2000) was obtained from Davisco (Le Sueur, Minn., USA). The protein was purified from sweet whey by ultra-filtration and ion exchange chromatography. The composition of the powder is 89.7% protein, 8.85% moisture, 1.36% ash (0.079% $Ca^{2+}$, 0.013% $Mg^{2+}$, 0.097% $K^+$, 0.576% $Na^+$, 0.050% $Cl^-$). All other reagents used were of analytical grade (Merck Darmstadt, Germany).

The protein solution was prepared at 0.2% concentration by solvation of β-lactoglobulin in MilliQ® water (Millipore), and stirring at 20° C. for 2 h. Then pH of aliquots was adjusted to 5.0, 5.2, 5.4, 5.6, 5.8, 6.0, 6.2, 6.4, 6.6, 6.8, 7.0 by HCl addition. The solutions were filled in 20 ml glass vials (Agilent Technologies) and sealed with aluminum capsules containing a silicon/PTFE sealing. The solutions were heated at 85° C. for 15 min (time to reach the temperature 2.30-3.00 min). After the heat treatment, the samples were cooled in ice water to 20° C.

The visual aspect of products (FIG. 1) indicates that the optimal pH of micellisation is 5.8.

Example 2

Micellisation of Whey Protein Isolate

Whey protein isolate (WPI) (Bipro®, Batch JE032-1-420) was obtained from Davisco (Le Sueur, Minn., USA). The composition of the powder is reported in table 1.

The protein solution was prepared at 3.4% protein by solvation of whey protein powder in MilliQ® water (Millipore), and stirring at 20° C. for 2 h. The initial pH was 7.2. Then pH of aliquots was adjusted at 5.6, 5.8, 6.0, 6.2, 6.4 and 6.6 by HCl 0.1N addition.

The solutions were filled in 20 ml glass vials (Agilent Technologies) and sealed with aluminum capsules containing a silicon/PTFE sealing. The solutions were heated at 85° C. for 15 min (time to reach the temperature 2.30-2.50 min). After the heat treatment, samples were cooled in ice water to 20° C.

The turbidity of heated whey proteins has been determined at 500 nm and 25° C., samples were diluted to allow the measurement in the range of 0.1-3 Abs unit (Spectrophotometer Uvikon 810, Kontron Instrument). Values were calculated for the initial protein concentration 3.4%.

The pH of micellisation was considered to be reached upon stability (less than 5% variation of the initial value) of the absorbance measured at 500 nm within an interval of 10 minutes for the same sample as illustrated by the FIG. 2. For this product the optimal pH for micellisation was 6.0 to 6.2. For this pH adjusted before heat treatment stable turbidity was 21 and residual soluble protein evaluated by absorbance at 280 nm after centrifugation was 1.9%. We can conclude that 45% of initial proteins were transformed in micelles at pH 6.0.

TABLE 2

Composition of WPI and sample characteristics after micellisation

| | |
|---|---|
| Supplier | Davisco |
| Product name | Bipro |
| Batch number | JE 032-1-420 |
| Composition (mg/100 g) | |
| Sodium | 650 |
| Potassium | 44 |
| Chloride*10 if ≤ 40 | 10 |
| Calcium | 82 |
| Phosphorus | 49 |
| Magnesium | 6 |
| Initial pH | 7.2 |
| pH micellisation | 6.0 |
| Turbidity (500 nm) for 3.4% protein in solution | 21 |
| Residual Soluble protein (%) by absorbance at 280 nm | 1.9 |

Example 3

Microscopic Observation of Micelles

Production of Micelles:

Protein solution was prepared at 2% protein by solvation of whey protein powder (WPI 90 batch 989/2, Lactalis, Retier, France) in MilliQ® water (Millipore), and stirred at 20° C. for 2 h. Then pHs of aliquots were adjusted using HCl 0.1N or NaOH 0.1N.

The solutions were filled in 20 ml glass vials (Agilent Technologies) and sealed with aluminum capsules containing a silicon/PTFE sealing. The solutions were heated at 85° C. for 15 min (time to reach the temperature 2.30-2.50 min). After the heat treatment, the samples were cooled in ice water to 20° C. For this product the optimal pH for micellisation was 7.4.

Microscopic Observations:

Liquid micelle samples were encapsulated in agar gel tubes. Fixation was achieved by immersion in a solution of 2.5% glutaraldehyde in 0.1M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples were embedded in Spurr resin (Spurr/ethanol 1:1, 2:1, 100%). After polymerization of the resin (70° C., 48 hours), semi-thin and ultra-thin sections were cut with a Leica ultracut UCT ultra-microtome. Ultra-thin sections, stained with aqueous uranyl-acetate and lead citrate, were examined in transmission electron microscopy (Philips CM12, 80 kV).

Figure 3:
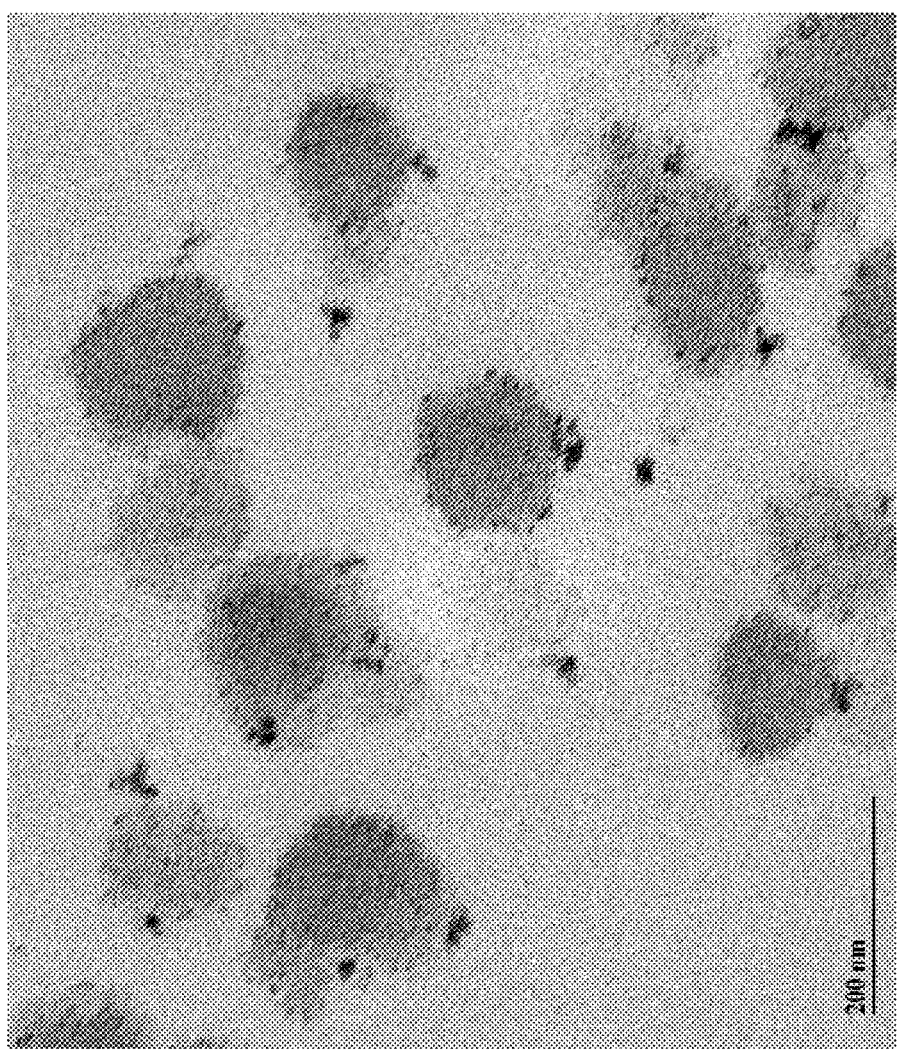
FIG. 3 is a Transmission Electron Microscopy micrograph from whey protein micelles (2 wt. %, WPI 95, Lactalis) at pH 7.4. Scale bar is 200 nm.

TEM micrograph is presented in FIG. 3. Obtained micelles are presenting a spherical shape with a diameter of 200 nm.

Particle Size Distribution

The intensity-based size distributions of micelles were measured for those micelles obtained by heat-treatment of a 1 wt % β-lactoglobulin dispersion for 15 min at 85° C. at pH 4.25 (positively charged with a zeta potential around +25 mV) and at pH 6.0 (negatively charged with a zeta potential around −30 mV). Z-averaged hydrodynamic diameter of the micelles was 229.3 mm at pH 4.25 an 227.2 at pH 6.0. β-LG and whey protein aggregations were followed using dynamic light scattering. A Nanosizer ZS apparatus (Malvern Instruments, UK) equipped with a laser emitting at 633 nm and with 4.0 mW power was used. The instrument was used in the backscattering configuration, where detection is done at a scattering angle of 173°. This allows considerable reduction of the multiple scattering signals found in turbid samples. Samples were placed in a squared quartz cell (Hellma, pathlength 1 cm). The path length of the light beam was automatically set by the apparatus, depending on the sample turbidity (attenuation). The autocorrelation function was calculated from the fluctuation of the scattered intensity). The results are presented in FIG. 6. It shows that the average particle is characterized by a very narrow polydispersity index (<0.200).

Example 4

Micellisation of a β-lactoglobulin at a Constant pH

The method described in example 1 was repeated with the proviso of using an aqueous solution of 2% β-lactoglobulin. The pH of this solution has been adjusted to 7.0 after adding Arginine HCl solutions to obtain a final salt concentration ranging from 5 to 200 mM and a final β-lactoglobulin concentration of 1%. Subsequent heat treatment (80° C., 10 min, about 2 min heating up) was carried out to produce micelles.

The results are shown in FIG. 4 and clearly indicate that only in the ionic strength range of from about 50 to 70 mM, a substantial turbidity can be observed, indicating the presence of whey protein micelles.

Example 5

Preparing a Whitening Agent

Native whey proteins (WPI 95 batch 848, Lactalis; 8 wt-% aqueous solution) were treated according to example 2. The resulting product lightness (L) was measured in trans-reflectance mode using a MacBeth CE-XTH D65 10° SCE apparatus equipped with a 2 mm measuring cell. The resulting lightness was L=74.8, that could be compared to the value of L=74.5 for full-fat milk.

Example 6

Preparing an Aqueous Foam

Native β-lactoglobulin (Biopure, Davisco, lot JE 002-8-922, 2 wt-% aqueous solution) was mixed with 120 mM Arginine HCl solution so that the final β-lactoglobulin concentration was 1 wt. % and Arginine HCl 60 mM. The pH was then adjusted to 7.0 by addition of 1N HCl. The mixture was then heat treated at 80° C. for 10 minutes so that 90% of initial β-lactoglobulin was converted into micelles having a z-averaged diameter of 130 nm. In this case, the diameter of the micelles was determined using a Nanosizer ZS apparatus (Malvern Instruments, UK). The sample was poured in a quartz cuvette and variations of the scattered light were recorded automatically. The obtained autocorrelation function was fitted using the cumulants method so that the diffusion coefficient of the particles could be calculated and thereafter the z-averaged hydrodynamic diameter using the Stokes-Einstein law. For this measurement, the refractive index of the solvent was taken as 1.33 and that of the micelles 1.45. A volume of 50 mL of the resulting dispersion of β-lactoglobulin micelles is then foamed by nitrogen sparging through a glass frit generating bubbles of 12-16 µm to produce a foam volume of 180 cm³ using the standardised Foamscan™ (ITConcept) apparatus. The volume stability of the foam was then followed with time at 26° C. using image analysis and compared to the stability of the foam obtained with β-lactoglobulin treated in the same conditions, but without Arginine HCl, where no micelles were formed. FIG. 5 shows that the foam volume stability is greatly improved by the presence of β-lactoglobulin micelles.

Example 7

Powdered Whey Protein Micelles Obtained by Spray-drying

Material
Whey protein isolate (WPI, Prolacta90® from Lactalis, Rétiers, France) with a protein content of 90%
Edible lactose
Maltodextrins DE39
De-ionised water
Edible hydrochloric acid 1M
Method
Using a double-jacketed 100 L tank, the Prolacta90® powder was dispersed at 50° C. in de-ionized water at a protein concentration of 10 wt % under gentle stirring in order to avoid foam formation, i.e. 11 kg of Prolacta90® were dispersed in 89 kg of de-ionised water. After 1 hour of dispersion, the pH of the dispersion was adjusted to the micellisation pH (around 6.3 in that case) by addition of HCl. The temperature of the dispersion was raised to 85° C. and maintained for 15 minutes in order to generate the whey protein micelles. After 15 minutes, the temperature was decreased to 50° C. and the 10 wt % whey protein micelles dispersion was split in two batches of 50 kg. In a first trial, 20 kg of lactose were dispersed in 50 kg of micelles dispersion at 50° C. and stirred for 30 min. Similarly, 20 kg of maltodextrins DE39 were added to the remaining 50 kg of whey protein micelles dispersion.

The two mixtures were then spray dried into a NIRO SD6.3N tower at a flow rate of 15 L/h. The air input temperature was 140° C. and the air output temperature was 80° C. The water content of the obtained powders was lower than 5%.

The size of the whey protein micelles was determined in presence of lactose and maltodextrin (DE39) in water using dynamic light scattering before and after spray drying. The total protein concentration was set to 0.4 wt % by dilution of the dispersion before spray drying or reconstitution of the powder in order to be in the dilute regime of viscosity for whey protein micelles. A Nanosizer ZS apparatus (Malvern Instruments) was used and micelle diameter was averaged from 20 measurements.

The particle diameter determined for whey protein micelles in presence of lactose and maltodextrins (DE39) was 310.4 nm and 306.6, respectively. After reconstitution of the powders, the respective diameters were found to be 265.3 nm and 268.5, respectively. These measurements confirm than whey protein micelles were physically stable regarding spray drying. The results were corroborated by TEM microscopy observations of 0.1 wt % whey protein micelles dispersions in water using negative staining in presence of 1% phosphotungstic acid at pH 7. A Philips CM12 transmission electron microscope operating at 80 kV was used. Whey protein micelles were observed in solution before spray drying and after reconstitution of the spray-dried powder. No difference of morphology and structure could be detected.

Example 8

Concentration by Evaporation

A whey protein isolate Prolacta 90 from Lactalis (lo 500648) has been reconstituted at 15° C. in soft water at a protein concentration of 4% to reach a final batch size of 2500 kg. The pH was adjusted by addition of 1M hydrochloric acid so that the final pH value was 5.90. The whey protein dispersion was pumped through plate-plate APV-mix heat exchanger at a flow rate of 500 l/h. Pre-heating at 60° C. was followed by heat treatment of 85° C. for 15 minutes. Formation of whey protein micelles was checked by measurement of particle size using dynamic light scattering as well a turbidity measurement at 500 nm. The obtained 4% whey protein micelles dispersion was characterised by a hydrodynamic radius of particles of 250 nm, a polydispersity index of 0.13 and a turbidity of 80. The whey protein micelle dispersion was then used to feed a Scheffers evaporator at a flow rate of 500 l/h. The temperature and vacuum in the evaporator were adapted so that around 500 kg whey protein micelles concentrate having a protein concentration 20% were produced and cooled down to 4° C.

Example 9

Enrichment by Microfiltration

A whey protein isolate Prolacta 90 from Lactalis (lo 500648) has been reconstituted at 15° C. in soft water at a protein concentration of 4% to reach a final batch size of 2500 kg. The pH was adjusted by addition of 1M hydrochloric acid so that the final pH value was 5.90. The whey protein dispersion was pumped through plate-plate APV-mix heat exchanger at a flow rate of 500 l/h. A pre-heating at 60° C. was followed by heat treatment of 85° C. for 15 minutes. Formation of whey protein micelles was checked by measurement of particle size using dynamic light scattering as well a turbidity measurement at 500 nm. The obtained 4% whey protein micelles dispersion was characterised by a hydrodynamic radius of particles of 260 nm, a polydispersity index of 0.07 and a turbidity of 80. The micelle form of the protein was also checked by TEM, and micelle structures with an average diameter of 150-200 nm were clearly visible (FIG. 9). The whey protein micelle dispersion could be cooled at 4° C. for storage or directly used to feed a filtration unit equipped with a 6.8 m² Carbosep M14 membrane at a flow rate of 180 l/h. In that case, the concentration of the whey protein micelles was performed at 10 to 70° C. until the permeate flow rate reached 70 l/h. In that case, the final whey protein concentrate contained 20% of proteins. The structure of the micelles in the concentrate was checked by TEM, and clearly no significant change was visible compared to the 4% whey protein dispersion before microfiltration (FIG. 10).

Example 10

Whey Protein Micelle Powder Comprising at Least 90% Whey Protein 200 kg of a whey protein micelle concentrate obtained by microfiltration at 20% protein (see example above) were injected in a Niro SD6.3N tower using an atomisation nozzle (Ø=0.5 mm, spraying angle=65°, pressure=40 bars) at a product flow rate of 25 kg/h. The inlet temperature of product was 150° C. and the outlet temperature was 75° C. The airflow in the tower was 150 m³/h. The moisture content in the powder was less than 4% and the powder was characterized by a very high flowability. Scanning electron microscopy of the powder exhibited very spherical particles having an apparent diameter ranging from 10 to 100 μm (FIG. 8).

Example 11

Mixed Whey Protein Micelle Powder 20 kg of a whey protein micelle concentrate were mixed with 1.7 kg of maltodextrins with a DE of 39 so that the final whey protein micelle to maltodextrin ratio in powder is 70/30. This mixture was injected in a Niro SD6.3N tower using an atomisation nozzle (Ø=0.5 mm, spraying angle=65°, pressure=40 bars) at a product flow rate of 25 kg/h. The inlet temperature of product was 150° C. and the outlet temperature was 75° C. The airflow in the tower was 150 m³/h. The moisture content in the powder was less than 4% and the powder was characterized by very high flow ability.

The powders of examples 10 and 11, when reconstituted in water, comprise essentially micelles having the same structure and morphology as the whey protein micelle concentrate.

Example 12

Recipe for a Cosmetic Composition Comprising 3.8% whey protein micelles. Exfoliating shower gel.

| ingredients | Percentages |
| --- | --- |
| rose distilled water | 35-40 |
| WPM 20% concentrated | 15-25 |
| Sulfosuccinate | 10-20 |
| Alkylsulfonate | 10-15 |
| Glycerin | 5-10 |
| Coco Betaine | 1-10 |
| Xanthan Gum | 0.1-2 |
| EDTA | 0.1-1 |
| Potassium sorbate | 0.1-1 |
| Fragrance | 0.1-1 |

Method:

WPM 20% concentrated and rose distilled water were warmed to 40° C. then glycerin and xanthan gum were added. This blend was added to alkyl sulfonate, Coco betaine, sulfosuccinate and EDTA. All ingredients were mixed by stirring, then potassium sorbate and fragrance were added.

Example 17

Recipe for a Cosmetic Composition Comprising 11.8% Whey Protein Micelles. WPM Peeling Lotion

| ingredients | % |
| --- | --- |
| WPM concentrated 20% | 55-65 |
| Almond oil | 15-20 |
| Glycerin | 5-10 |
| Fragrance | 1-10 |
| Cetyl Alcohol | 1-5 |
| Stearic Acid | 1-5 |
| Polysorbate 60 | 1-5 |
| Propil trimonium | 1-5 |
| Paraben-DU | 0.1-5 |

Method:

WPM 20% concentrated was warmed to 70° C. then Glycerine was added. Melted (70° C.) oily phase (almond oil, cetyl alcohol stearic acid and polysorbate 60) was added and stirred until homogenous dispersion was obtained. The blend was cool down at room temperature then Paraben DU and Fragrance were added.

Example 18

Recipe for a Cosmetic Composition Comprising 14% Whey Protein Micelles. Wpm Peeling Lotion.

| ingredients | % |
|---|---|
| WPM 20% concentrated | 60-80 |
| Glycerin | 5-10 |
| soybean oil | 5-10 |
| propyltrimonium | 2-8 |
| Coco Betaine | 1-5 |
| CreamMaker Wax | 1-5 |
| Ceteareth-20 | 1-5 |
| Cetyl Alcohol | 1-5 |
| Paraben -DU | 0.1-2 |
| Fragrance | 0.1-1 |

Method:
WPM 20% concentrate were warmed to 70° C. then glycerin and propyltrimonium were added. Melted (70° C.) oily phase (soybean oil, Cream Maker WAX, ceteareth-20, coco betaine, cetyl alcohol) was added and stirred until homogenous dispersion was obtained. The blend was cool down at room temperature then Paraben-DU and Fragrance were added.

The invention claimed is:

1. A cosmetic composition comprising whey protein micelles consisting essentially of spherical agglomerates of denatured whey protein in an amount effective to act as an abrasive medium for abrading skin, at least 80% of the whey protein micelles have a size smaller than 1 micron, and the whey protein micelles have an average size in the range of 100nm to 900nm, wherein the whey protein micelles are obtainable by treating a demineralized aqueous solution of native whey protein either by (i) adjusting the pH of the solution to between 3.5 and 9 or by (ii) adjusting the ionic strength of the solution while keeping the pH constant; and then by heating the solution with the adjusted pH or ionic strength to a temperature of about 70° C. to 95° C. for a time period between 12 to 25 minutes.

2. The cosmetic composition of claim 1, wherein the whey protein micelles are in aggregates that have an average size of greater than 1 μm and are contained in the composition in an amount of at least 1% up to 50% by weight of the composition.

3. The cosmetic composition of claim 1, wherein aggregates of the whey protein micelles are present, and the aggregates are combined with one or more active agents.

4. The cosmetic composition of claim 3, wherein the active agents are one or more of peptides, plant extracts, protein hydrolysates, bioactives, vitamins, minerals, pharmaceuticals, cosmetic components or mixtures thereof.

5. The cosmetic composition of claim 1, which further comprises one or more of soluble or non-soluble salts, pigments, fats, emulsifiers, aroma, plant extracts, ligands, bioactives, minerals, vitamins, drugs, or any mixture thereof.

6. The cosmetic composition of claim 1, wherein the whey protein micelles are present in form of a liquid dispersion, a suspension, a gel, a cream or a powder and at a concentration of whey protein that is 10% to 50% by weight of the composition.

7. The cosmetic composition of claim 1, wherein the whey protein micelles have an average size in the range of 200nm to 400nm, and at least 80% of the whey protein micelles have dimensions between 100nm and 700nm.

8. The cosmetic composition of claim 1, wherein the whey protein micelles are present in the composition in an amount sufficient to also act as a whitening agent.

9. The cosmetic composition of claim 1, wherein the whey protein micelles are present in the composition in an amount sufficient to also stabilize fat or air to thus serve as one or more of an emulsifier, a whitening agent, a fat substitute, a substitute for micellar casein, or a foaming agent for the composition.

10. The cosmetic composition of claim 1 in the form of a solution, a cream, a gel, a paste, a foam, or a spray.

11. The cosmetic composition of claim 1 in the form of a shampoo, a shower gel or other body or hair care product.

12. The cosmetic composition of claim 1, wherein the protein micelles are present as aggregates.

13. The cosmetic composition of claim 1, wherein the solution with the adjusted pH or ionic strength is heated to a temperature of about 70° C. to 95° C. for 12 to 20 minutes.

14. The cosmetic composition of claim 1, wherein the solution with the adjusted pH or ionic strength is heated to a temperature of about 82° C. to 89° C.

15. A cosmetic composition comprising an abrasive medium comprising whey protein micelles consisting essentially of spherical agglomerates of denatured whey protein and having an average size in the range of 100nm to 900nm and which are contained in the composition in an amount of from 1% to 50% by weight of the composition to act as an abrasive for abrading skin, at least 80% of the whey protein micelles have a size smaller than 1 micron; wherein the cosmetic composition also contains an active agent of a plant extract and a vitamin, and the composition is in the form of a liquid dispersion, a suspension, a gel, a cream, a paste, a foam, a spray or a powder, wherein the whey protein micelles are obtainable by treating a demineralized aqueous solution of native whey protein either by (i) adjusting the pH of the solution to between 3.5 and 9 or by (ii) adjusting the ionic strength of the solution while keeping the pH constant; and then by heating the solution with the adjusted pH or ionic strength to a temperature of about 70° C. to 95° C. for a time period between 12 to 25 minutes.

16. The cosmetic composition of claim 15, wherein the whey protein micelles are present in the composition in an amount sufficient to also stabilize fat or air to thus serve as one or more of an emulsifier, a whitening agent, a fat substitute, a substitute for micellar casein, or a foaming agent for the composition.

17. The cosmetic composition of claim 15, wherein the whey protein micelles are present in the composition in the form of aggregates and in an amount of 10% to 50% by weight, with the micelles having hydrophilic and hydrophobic parts, with the aggregates having inner cores and outer parts, wherein the hydrophilic parts are oriented towards the outer parts while the hydrophobic parts are oriented towards the inner cores to provide stability to the micelle aggregates in a hydrophilic environment.

18. The cosmetic composition of claim 15, wherein the whey protein micelles are coated with one of an emulsifier of a phospholipid, or a coating agent of acacia gum or an emulsifier selected from the group consisting of sulphated butyl oleate, diacetyltartaric acid esters of mono- and diglycerides, citric acid esters of monoglycerides, stearoyl lactylates and mixtures thereof.

19. The cosmetic composition of claim 15, wherein the solution with the adjusted pH or ionic strength is heated to a temperature of about 70° C. to 95° C. for about 15 minutes.

20. The cosmetic composition of claim 15, wherein the solution with the adjusted pH or ionic strength is heated to a temperature of about 82° C. to 89° C.

21. A method of treating skin which comprises topically applying the cosmetic composition of claims 1 or 15 to the skin of a subject.

22. The method of claim 21, wherein the whey protein micelles are in the form of a liquid dispersion, a suspension, a cream, a gel or a powder.

23. The method of claim 21, wherein the protein micelles are present as aggregates.

24. A method for the manufacture of the cosmetic composition of claims 1 or 15, which comprises incorporating the protein micelles or aggregates thereof into a cosmetic composition, wherein the protein micelles or aggregates thereof are added in an amount sufficient to enable the composition to act as an abrasive medium on skin.

25. The method of claim 24, wherein the protein micelles are whey protein micelles and are present in the composition in an amount sufficient to also stabilize fat or air to thus serve as one or more of an emulsifier, a whitening agent, a fat substitute, a substitute for micellar casein, or a foaming agent for the composition.

* * * * *